(12) United States Patent
Revel et al.

(10) Patent No.: US 7,264,945 B2
(45) Date of Patent: Sep. 4, 2007

(54) IFN RECEPTOR 1 BINDING PROTEINS, DNA ENCODING THEM, AND METHODS OF MODULATING CELLULAR RESPONSE TO INTERFERONS

(75) Inventors: Michel Revel, Rehovot (IL); Carolina Abramovitch, Yavne (IL); Judith E. Chebath, Rehovot (IL)

(73) Assignee: Yeda Research and Development Co. Ltd, Rehovot (IL)

( * ) Notice: Subject to any disclaimer, the term of this patent is extended or adjusted under 35 U.S.C. 154(b) by 506 days.

(21) Appl. No.: 10/309,280

(22) Filed: Dec. 4, 2002

(65) Prior Publication Data

US 2003/0176678 A1  Sep. 18, 2003

Related U.S. Application Data

(63) Continuation of application No. 09/341,640, filed as application No. PCT/US98/00671 on Jan. 15, 1998, now abandoned.

(60) Provisional application No. 60/035,636, filed on Jan. 15, 1997.

(51) Int. Cl.
*C12N 15/00* (2006.01)
*C12N 5/00* (2006.01)

(52) U.S. Cl. ............... 435/69.1; 435/70.1; 435/320.1; 435/325

(58) Field of Classification Search .................. None
See application file for complete search history.

(56) References Cited

U.S. PATENT DOCUMENTS 5,981,181 A * 11/1999 Frommer et al. ............. 435/6
6,242,587 B1 * 6/2001 Naik et al. ................. 536/23.5

FOREIGN PATENT DOCUMENTS

EP    0 679 717 A2   11/1995
WO    WO98/14471 A1   4/1998

* cited by examiner

*Primary Examiner*—Christine J. Saoud
*Assistant Examiner*—Jegatheesan Seharaseyon
(74) *Attorney, Agent, or Firm*—Browdy and Neimark, PLLC

(57) ABSTRACT

Novel proteins IR1B1 and IR1B4 have been isolated which bind to the type I IFN receptor IFNAR1 and function in the cellular response to IFNs. DNA encoding such proteins in either the sense or anti-sense orientation can be administered to either enhance or inhibit the cellular response to IFNs. Antibodies to the proteins can be used for isolation of the new protein or for immunodetection thereof.

11 Claims, 13 Drawing Sheets

FIG. 2

| Number | pACT | pAS or pGBT10 | Number | pACT | pAS or pGBT10 |
|---|---|---|---|---|---|
| 1 | IR1B4 | vector | 5 | IR1B4 | tat |
| 2 | IR1B4 | p53 | 6 | IR1B4 | rev |
| 3 | IR1B4 | IFNAR1-IC | 7 | - | lacZ, control - |
| 4 | IR1B4 | cdk | 8 | IR1B4 | lamin |

FIG. 3

```
CGT CTC GAG GCG AGT TGG CGG AGC TGT GCG CGC GGC GGG GCG ATG GGG GGC TCG GGC AGT   60
                                                        MET GLY GLY SER GLY SER

CGC CTG TCC AAG GAG CTG CTG GCC GAG TAC CAG GAC TTG ACG TTC CTG ACG AAG CAG GAG  120
ARG LEU SER LYS GLU LEU LEU ALA GLU TYR GLN ASP LEU THR PHE LEU THR LYS GLN GLU

ATC CTC CTA GCC CAC AGG CGG TTT TGT GAG CTG CTT CCC CAG GAG CAG CGG AGC GTG GAG  180
ILE LEU LEU ALA HIS ARG ARG PHE CYS GLU LEU LEU PRO GLN GLU GLN ARG SER VAL GLU

TCG TCA CTT CGG GCA CAA GTG CCC TTC GAG CAG ATT CTC AGC CTT CCA GAG CTC AAG GCC  240
SER SER LEU ARG ALA GLN VAL PRO PHE GLU GLN ILE LEU SER LEU PRO GLU LEU LYS ALA

AAC CCC TTC AAG GAG CGA ATC TGC AGG GTC TTC TCC ACA TCC CCA GCC AAA GAC AGC CTT  300
ASN PRO PHE LYS GLU ARG ILE CYS ARG VAL PHE SER THR SER PRO ALA LYS ASP SER LEU

AGC TTT GAG GAC TTC CTG GAT CTC CTC AGT GTG TTC AGT GAC ACA GCC ACG CCA GAC ATC  360
SER PHE GLU ASP PHE LEU ASP LEU LEU SER VAL PHE SER ASP THR ALA THR PRO ASP ILE

AAG TCC CAT TAT GCC TTC CGC ATC TTT GAC TTT GAT GAT GAC GGA ACC TTG AAC AGA GAA  420
LYS SER HIS TYR ALA PHE ARG ILE PHE ASP PHE ASP ASP ASP GLY THR LEU ASN ARG GLU

GAC CTG AGC CGG CTG GTG AAC TGC CTC ACG GGA GAG GGC GAG GAC ACA CGG CTT AGT GCG  480
ASP LEU SER ARG LEU VAL ASN CYS LEU THR GLY GLU GLY GLU ASP THR ARG LEU SER ALA

TCT GAG ATG AAG CAG CTC ATC GAC TAC ATC CTG GAA GAG TCT GAC ATT GAC AGG GAT GGA  540
SER GLU MET LYS GLN LEU ILE ASP TYR ILE LEU GLU GLU SER ASP ILE ASP ARG ASP GLY

ACC ATC AAC CTC TCT GAG TTC CAG CAC GTC ATC TCC CGT TCT CCA GAC TTT GCC AGC TCC  600
THR ILE ASN LEU SER GLU PHE GLN HIS VAL ILE SER ARG SER PRO ASP PHE ALA SER SER

TTT AAG ATT GTC CTG TGA CAG CAG CCC CAG CGT GTG TCC TGG CAC CCT GTC CAA GAA CCT  660
PHE LYS ILE VAL LEU

TTC TAC TGC TGA GCT GTG GCC AAG GTC AAG CCT GTG TTG CCA GTG CGG GCC AAG CTG GCC  720
CAG CCT GGA GCT GGC GCT GTG CAG CCT CAC CCC GGG CAG GGG CGG CCC TCG TTG TCA GGG  780
CCT CTC CTC ACT GCT GTT GTC ATT GCT CCG TTT GTG GGC CTT CGT GGC CA             830
```

FIG. 4

Alignment of IR1B1 with Calcineurin B (Calb) and Caltractin (Catr):

```
IR1B1
CALB         MGGSGSRLSKELLAEYQDLTFLTKQEILLAH
CATR                                 GNEASYPLEMCSHFDA
                                     MASNFKKANMASSSQRKRMSPKPELTE

IR1B1   32  RRFCELLPQEQRSVESSLRAQVPFFEQILSLPELKANPFKERICRVFSTSP
                  ::           ::
CALB    17  DEIKRLGKRFKKLDLDNSGSLSVEEF.MSLPELQQNPL...VQRVIDIF.
CATR    28  EQKQEIREAFDLFDADGTGTIDVKELKVAMRALGFEPKKEEIKKMISEI.

IR1B1   82  AKDSLSFEDFLDLLSVFSDTAT.PDIKS..HYAFRIFDFDDDGTLNREDLS
                                    ::
CALB    62  DTDGNGEVDFKEFIEGVSQFSVKGDKEQKLRFAFRIYDMDKDGYISNGELF
CATR    62  DKEGTGKMNFGDFLTVMTQKMSEKDTKEEILKAFKLFDDDETGKISFKNLK

IR1B1  130  RLVNCLTGEGEDTRLSASAEMKQLIDYILEESDIDRDGTINLSEFQHVI
       125  :
CALB   113  QVLKMMVGNNLKDTQLQQIVDKTIIN....ADKDGDGRISFEEFCAVV
CATR   128  RVAKEL.GENLTDEELQEMIDE........ADRDGDGEVSEQEFLRIM

IR1B1  178  SRSPDFASSFKIVL  191
CALB   157  GGLDIHKKMVVDV   169
CATR   167  KKTSLY          172
```

FIG. 7

```
   1 GCC GCG AAC TGC ATC ATG GAG AAT TTT GTA GCC ACC TTG GCT   42
                             M   E   N   F   V   A   T   L   A
  43 AAT GGG ATG AGC CTC CAG CCG CCT CTT GAA GAA GTG TCC TGT   84
      N   G   M   S   L   Q   P   P   L   E   E   V   S   C
  85 GGC CAG GCG GAA AGC AGT GAG AAG CCC AAC GCT GAG GAC ATG  126
      G   Q   A   E   S   S   E   K   P   N   A   E   D   M
 127 ACA TCC AAA GAT TAC TAC TTT GAC TCC TAC GCA CAC TTT GGC  168
      T   S   K   D   Y   Y   F   D   S   Y   A   H   F   G
 169 ATC CAC GAG GAG ATG CTG AAG GAC GAG GTG CGC ACC CTC ACT  210
      I   H   E   E   M   L   K   D   E   V   R   T   L   T
 211 TAC CGC AAC TCC ATG TTT CAT AAC CGG CAC CTC TTC AAG GAC  252
      Y   R   N   S   M   F   H   N   R   H   L   F   K   D
 253 AAG GTG GTG CTG GAC GTC GGC TCG GGC ACC GGC ATC CTC TGC  294
      K   V   V   L   D   V   G   S   G   T   G   I   L   C
 295 ATG TTT GCT GCC AAG GCC GGG GCC CGC AAG GTC ATC GGG ATC  336
      M   F   A   A   K   A   G   A   R   K   V   I   G   I
 337 GAG TGT TCC AGT ATC TCT GAT TAT GCG GTG AAG ATC GTC AAA  378
      E   C   S   S   I   S   D   Y   A   V   K   I   V   K
 379 GCC AAC AAG TTA GAC CAC GTG GTG ACC ATC ATC AAG GGG AAG  420
      A   N   K   L   D   H   V   V   T   I   I   K   G   K
 421 GTG GAG GAG GTG GAG CTC CCA GTG GAG AAG GTG GAC ATC ATC  462
      V   E   E   V   E   L   P   V   E   K   V   D   I   I
 463 ATC AGC GAG TGG ATG GGC TAC TGC CTC TTC TAC GAG TCC ATG  504
      I   S   E   W   M   G   Y   C   L   F   Y   E   S   M
 505 CTC AAC ACC GTG CTC TAT GCC CGG GAC AAG TGG CTG GCG CCC  546
      L   N   T   V   L   Y   A   R   D   K   W   L   A   P
 547 GAT GGC CTC ATC TTC CCA GAC CGG GCC ACG CTG TAT GTG ACG  588
      D   G   L   I   F   P   D   R   A   T   L   Y   V   T
 589 GCC ATC GAG GAC CGG CAG TAC AAA GAC TAC AAG ATC CAC TGG  630
      A   I   E   D   R   Q   Y   K   D   Y   K   I   H   W
 631 TGG GAG AAC GTG TAT GGC TTC GAC ATG TCT TGC ATC AAA GAT  672
      W   E   N   V   Y   G   F   D   M   S   C   I   K   D
 673 GTG GCC ATT AAG GAG CCC CTA GTG GAT GTC GTG GAC CCC AAA  714
      V   A   I   K   E   P   L   V   D   V   V   D   P   K
 715 CAG CTG GTC ACC AAC GCC TGC CTC ATA AAG GAG GTG GAC ATC  756
      Q   L   V   T   N   A   C   L   I   K   E   V   D   I
 757 TAT ACC GTC AAG GTG GAA GAC CTG ACC TTC ACC TCC CCG TTC  798
      Y   T   V   K   V   E   D   L   T   F   T   S   P   F
 799 TGC CTG CAA GTG AAG CGG AAT GAC TAC GTG CAC GCC CTG GTG  840
      C   L   Q   V   K   R   N   D   Y   V   H   A   L   V
 841 GCC TAC TTC AAC ATC GAG TTC ACA CGC TGC CAC AAG AGG ACC  882
      A   Y   F   N   I   E   F   T   R   C   H   K   R   T
 883 GGC TTC TCC ACC AGC CCC GAG TCC CCG TAC ACG CAC TGG AAG  924
      G   F   S   T   S   P   E   S   P   Y   T   H   W   K
 925 CAG ACG GTG TTC TAC ATG GAG GAC TAC CTG ACC GTG AAG ACG  966
      Q   T   V   F   Y   M   E   D   Y   L   T   V   K   T
 967 GGC GAG GAG ATC TTC GGC ACC ATC GGC ATG CGG CCC AAC GCC 1008
      G   E   E   I   F   G   T   I   G   M   R   P   N   A
1009 AAG AAC AAC CGG GAC CTG GAC TTC ACC ATC GAC CTG GAC TTC 1050
      K   N   N   R   D   L   D   F   T   I   D   L   D   F
1051 AAG GGC CAG CTG TGC GAG CTG TCC TGC TCC ACC GAC TAC CGG 1092
      K   G   Q   L   C   E   L   S   C   S   T   D   Y   R
1093 ATG CGC TGA GGC CCG GCT CTC CCG CCC TGC ACG AGC CCA GGG 1134
      M   R
1135 GCT GAG CGT TCC TAG GCG GTT TCG GGC TCC CCC TTC CTC TC  1176
1177 CCT CCC TCC CGC AGA AGG GGG TTT AGG GGC CTG GGC TGG G   1218
1219 GGA TGG GGA GGG CAC ATT GGG ACT GTG TTT TTC ATA AAT TAT 1260
1261 GTT TTT ATA TGG TTG CAT TTA ATG CCA ATA AAT CCT CAG CTG 1302
1303 GGG AAA                                                 1308
```

FIG. 8

```
              10         20         30         40         50         60
IR1B4   MENFVATLANGMSLQPPLEEVSCGQAESSEKPNAEDMTSKDYYFDSYAHFGIHEEMLKDE
        ::                ::::::::::::::::::::::::::::::::::::::::::
PRMT1   MA--------AAEAANCIMEVSCGQAESSEKPNAEDMTSKDYYFDSYAHFGIHEEMLKDE
                         10        20        30        40        50

70         80         90        100        110        120
IR1B4   VRTLTYRNSMFHNRHLFKDKVVLDVGSGTGILCMFAAKAGARKVIGIECSSISDYAVKIV
        ::::::::::::::::::::::::::::::::::::::::::::::::::::::::::::
PRMT1   VRTLTYRNSMFHNRHLFKDKVVLDVGSGTGILCMFAAKAGARKVIGIECSSISDYAVKIV
              60         70         80         90        100        110

130        140        150        160        170        180
IR1B4   KANKLDHVVTIIKGKVEEVELPVEKVDIIISEWMGYCLFYESMLNTVLYARDKWLAPDGL
        ::::::::::::::::::::::::::::::::::::::::::::::::::::::::::::
PRMT1   KANKLDHVVTIIKGKVEEVELPVEKVDIIISEWMGYCLFYESMLNTVLYARDKWLAPDGL
             120        130        140        150        160        170

190        200        210        220        230        240
IR1B4   IFPDRATLYVTAIEDRQYKDYKIHWWENVYGFDMSCIKDVAIKEPLVDVVDPKQLVTNAC
        ::::::::::::::::::::::::::::::::::::::::::::::::::::::::::::
PRMT1   IFPDRATLYVTAIEDRQYKDYKIHWWENVYGFDMSCIKDVAIKEPLVDVVDPKQLVTNAC
             180        190        200        210        220        230

250        260        270        280        290        300
IR1B4   LIKEVDIYTVKVEDLTFTSPFCLQVKRNDYVHALVAYFNIEFTRCHKRTGFSTSPESPYT
        ::::::::::::::::::::::::::::::::::::::::::::::::::::::::::::
PRMT1   LIKEVDIYTVKVEDLTFTSPFCLQVKRNDYVHALVAYFNIEFTRCHKRTGFSTSPESPYT
             240        250        260        270        280        290

310        320        330        340        350        360
IR1B4   HWKQTVFYMEDYLTVKTGEEIFGTIGMRPNAKNNRDLDFTIDLDFKGQLCELSCSTDYRMR
        ::::::::::::::::::::::::::::::::::::::::::::::::::::::::::::
PRMT1   HWKQTVFYMEDYLTVKTGEEIFGTIGMRPNAKNNRDLDFTIDLDFKGQLCELSCSTDYRMR
             300        310        320        330        340        350
```

FIG. 9

```
IR1B4          MENFVATLANGMSLQPPLEEVSCGQAESSEKPNAEDMTSKDYYFDSYAHFGIHEEMLKDE
HCP-1          MENFVATLANGMSLQPPLEEVSCGQAESSEKPNAEDMTSKDYYFDSYAHFGIHEEMLKDE

IR1B4          VRTLTYRNSMFHNRHLFKDKVVLDVGSGTGILCMFAAKAGARKVIGIECSSISDYAVKIV
HCP-1          VRTLTYRNSMFHNRHLFKDKVVLDVGSGTGILCMFAAKAGARKVIGIVCSSISDYAVKIV

IR1B4          KANKLDHVVTIIKGKVEEVELPVEKVDIII-SEWMGYCLFYESMLNTVLYARDKWLAPDG
HCP-1          KANKLDHVVTIIKGKVEEVELPVEKVASSSASGWATASSTSPCSM--PGTSVAPDG

IR1B4          LIFPDRATLYVTAIEDRQYKDYKIHWWENVYGFDMSCIKDVAIKEPLVDVVDPKQLVTNA
HCP-1          LIFPDRATLYVTAIEDRQYKDYKIHWWENVYGFDMSCIKDVAIKEPLVDVVDPKQLVTNA

IR1B4          CLIKEVDIYTVKVEDLTFTSPFCLQVKRNDYVHALVAYFNIEFTRCHKRTGFSTSPESPY
HCP-1          CLIKEVDIYTVKVEDLTFTSPFCLQVKRNDYVHALVAYFNIEFTRCHKRTGFSTSPESPY

IR1B4          THWKQTVFYMEDYLTVKTGEEIFGTIGMRPNAKNNRDLDFTIDLDFKGQLCELSCSTDYRMR
HCP-1          THWKQTVFYMEDYLTVKTGEEIFGTIGMRPNAKNNRDLDFTIDLDFKGQLCELSCSTDYRMR
```

Oligonucleotide:     None   Anti sense   Sense

Lane                  1         2          3

Peptide R1

SEQUENCE LISTING

<160> NUMBER OF SEQ ID NOS: 13

<210> SEQ ID NO 1
<211> LENGTH: 830
<212> TYPE: DNA
<213> ORGANISM: Homo sapiens
<220> FEATURE:
<221> NAME/KEY: CDS
<222> LOCATION: (43)..(615)
<223> OTHER INFORMATION:

<400> SEQUENCE: 1

```
cgtctcgagg cgagttggcg gagctgtgcg cgcggcgggg cg atg ggg ggc tcg         54
                                              Met Gly Gly Ser
                                              1 ggc agt cgc ctg tcc aag gag ctg ctg gcc gag tac cag gac ttg acg       102
Gly Ser Arg Leu Ser Lys Glu Leu Leu Ala Glu Tyr Gln Asp Leu Thr
5               10                  15                  20 ttc ctg acg aag cag gag atc ctc cta gcc cac agg cgg ttt tgt gag       150
Phe Leu Thr Lys Gln Glu Ile Leu Leu Ala His Arg Arg Phe Cys Glu
            25                  30                  35 ctg ctt ccc cag gag cag cgg agc gtg gag tcg tca ctt cgg gca caa       198
Leu Leu Pro Gln Glu Gln Arg Ser Val Glu Ser Ser Leu Arg Ala Gln
        40                  45                  50 gtg ccc ttc gag cag att ctc agc ctt cca gag ctc aag gcc aac ccc       246
Val Pro Phe Glu Gln Ile Leu Ser Leu Pro Glu Leu Lys Ala Asn Pro
    55                  60                  65 ttc aag gag cga atc tgc agg gtc ttc tcc aca tcc cca gcc aaa gac       294
Phe Lys Glu Arg Ile Cys Arg Val Phe Ser Thr Ser Pro Ala Lys Asp
70                  75                  80 agc ctt agc ttt gag gac ttc ctg gat ctc ctc agt gtg ttc agt gac       342
Ser Leu Ser Phe Glu Asp Phe Leu Asp Leu Leu Ser Val Phe Ser Asp
85                  90                  95                 100 aca gcc acg cca gac atc aag tcc cat tat gcc ttc cgc atc ttt gac       390
Thr Ala Thr Pro Asp Ile Lys Ser His Tyr Ala Phe Arg Ile Phe Asp
                105                 110                 115 ttt gat gat gac gga acc ttg aac aga gaa gac ctg agc cgg ctg gtg       438
Phe Asp Asp Asp Gly Thr Leu Asn Arg Glu Asp Leu Ser Arg Leu Val
            120                 125                 130 aac tgc ctc acg gga gag ggc gag gac aca cgg ctt agt gcg tct gag       486
Asn Cys Leu Thr Gly Glu Gly Glu Asp Thr Arg Leu Ser Ala Ser Glu
        135                 140                 145 atg aag cag ctc atc gac tac atc ctg gaa gag tct gac att gac agg       534
Met Lys Gln Leu Ile Asp Tyr Ile Leu Glu Glu Ser Asp Ile Asp Arg
    150                 155                 160 gat gga acc atc aac ctc tct gag ttc cag cac gtc atc tcc cgt tct       582
Asp Gly Thr Ile Asn Leu Ser Glu Phe Gln His Val Ile Ser Arg Ser
165                 170                 175                 180 cca gac ttt gcc agc tcc ttt aag att gtc ctg tgacagcagc cccagcgtgt     635
Pro Asp Phe Ala Ser Ser Phe Lys Ile Val Leu
                185                 190 gtcctggcac cctgtccaag aacctttcta ctgctgagct gtggccaagg tcaagcctgt     695
gttgccagtg cgggccaagc tggcccagcc tggagctggc gctgtgcagc ctcaccccgg     755
gcaggggcgg ccctcgttgt cagggcctct cctcactgct gttgtcattg ctccgtttgt     815
```

-continued gggccttcgt ggcca 830

<210> SEQ ID NO 2
<211> LENGTH: 191
<212> TYPE: PRT
<213> ORGANISM: Homo sapiens

<400> SEQUENCE: 2

Met Gly Gly Ser Gly Ser Arg Leu Ser Lys Glu Leu Leu Ala Glu Tyr
1               5                   10                  15

Gln Asp Leu Thr Phe Leu Thr Lys Gln Glu Ile Leu Leu Ala His Arg
            20                  25                  30

Arg Phe Cys Glu Leu Leu Pro Gln Glu Gln Arg Ser Val Glu Ser Ser
        35                  40                  45

Leu Arg Ala Gln Val Pro Phe Glu Gln Ile Leu Ser Leu Pro Glu Leu
    50                  55                  60

Lys Ala Asn Pro Phe Lys Glu Arg Ile Cys Arg Val Phe Ser Thr Ser
65                  70                  75                  80

Pro Ala Lys Asp Ser Leu Ser Phe Glu Asp Phe Leu Asp Leu Leu Ser
                85                  90                  95

Val Phe Ser Asp Thr Ala Thr Pro Asp Ile Lys Ser His Tyr Ala Phe
            100                 105                 110

Arg Ile Phe Asp Phe Asp Asp Gly Thr Leu Asn Arg Glu Asp Leu
        115                 120                 125

Ser Arg Leu Val Asn Cys Leu Thr Gly Glu Gly Glu Asp Thr Arg Leu
    130                 135                 140

Ser Ala Ser Glu Met Lys Gln Leu Ile Asp Tyr Ile Leu Glu Glu Ser
145                 150                 155                 160

Asp Ile Asp Arg Asp Gly Thr Ile Asn Leu Ser Glu Phe Gln His Val
                165                 170                 175

Ile Ser Arg Ser Pro Asp Phe Ala Ser Ser Phe Lys Ile Val Leu
            180                 185                 190

<210> SEQ ID NO 3
<211> LENGTH: 170
<212> TYPE: PRT
<213> ORGANISM: Artificial Sequence
<220> FEATURE:
<223> OTHER INFORMATION: synthetic

<400> SEQUENCE: 3

Met Gly Asn Glu Ala Ser Tyr Pro Leu Glu Met Cys Ser His Phe Asp
1               5                   10                  15

Ala Asp Glu Ile Lys Arg Leu Gly Lys Arg Phe Lys Lys Leu Asp Leu
            20                  25                  30

Asp Asn Ser Gly Ser Leu Ser Val Glu Glu Phe Met Ser Leu Pro Glu
        35                  40                  45

Leu Gln Gln Asn Pro Leu Val Gln Arg Val Ile Asp Ile Phe Asp Thr
    50                  55                  60

Asp Gly Asn Gly Glu Val Asp Phe Lys Glu Phe Ile Glu Gly Val Ser
65                  70                  75                  80

Gln Phe Ser Val Lys Gly Asp Lys Glu Gln Lys Leu Arg Phe Ala Phe
                85                  90                  95

Arg Ile Tyr Asp Met Asp Lys Asp Gly Tyr Ile Ser Asn Gly Glu Leu
            100                 105                 110

Phe Gln Val Leu Lys Met Met Val Gly Asn Asn Leu Lys Asp Thr Gln
        115                 120                 125

```
Leu Gln Gln Ile Val Asp Lys Thr Ile Ile Asn Ala Asp Lys Asp Gly
        130                 135                 140

Asp Gly Arg Ile Ser Phe Glu Phe Cys Ala Val Val Gly Gly Leu
145                 150                 155                 160

Asp Ile His Lys Lys Met Val Val Asp Val
                165                 170

<210> SEQ ID NO 4
<211> LENGTH: 172
<212> TYPE: PRT
<213> ORGANISM: Artificial Sequence
<220> FEATURE:
<223> OTHER INFORMATION: synthetic

<400> SEQUENCE: 4

Met Ala Ser Asn Phe Lys Lys Ala Asn Met Ala Ser Ser Ser Gln Arg
1               5                   10                  15

Lys Arg Met Ser Pro Lys Pro Glu Leu Thr Glu Glu Gln Lys Gln Glu
            20                  25                  30

Ile Arg Glu Ala Phe Asp Leu Phe Asp Ala Asp Gly Thr Gly Thr Ile
        35                  40                  45

Asp Val Lys Glu Leu Lys Val Ala Met Arg Ala Leu Gly Phe Glu Pro
    50                  55                  60

Lys Lys Glu Glu Ile Lys Lys Met Ile Ser Glu Ile Asp Lys Glu Gly
65                  70                  75                  80

Thr Gly Lys Met Asn Phe Gly Asp Phe Leu Thr Val Met Thr Gln Lys
                85                  90                  95

Met Ser Glu Lys Asp Thr Lys Glu Glu Ile Leu Lys Ala Phe Lys Leu
            100                 105                 110

Phe Asp Asp Asp Glu Thr Gly Lys Ile Ser Phe Lys Asn Leu Lys Arg
        115                 120                 125

Val Ala Lys Glu Leu Gly Glu Asn Leu Thr Asp Glu Glu Leu Gln Glu
    130                 135                 140

Met Ile Asp Glu Ala Asp Arg Asp Gly Asp Gly Glu Val Ser Glu Gln
145                 150                 155                 160

Glu Phe Leu Arg Ile Met Lys Lys Thr Ser Leu Tyr
                165                 170

<210> SEQ ID NO 5
<211> LENGTH: 31
<212> TYPE: DNA
<213> ORGANISM: Artificial Sequence
<220> FEATURE:
<223> OTHER INFORMATION: synthetic

<400> SEQUENCE: 5
ctgaggatcc aaagtcttct tgagatgcat c                              31

<210> SEQ ID NO 6
<211> LENGTH: 25
<212> TYPE: DNA
<213> ORGANISM: Artificial Sequence
<220> FEATURE:
<223> OTHER INFORMATION: synthetic

<400> SEQUENCE: 6
tgacgaattc ctatcataca aagtc                                     25

<210> SEQ ID NO 7
```

<211> LENGTH: 1308
<212> TYPE: DNA
<213> ORGANISM: Homo sapiens
<220> FEATURE:
<221> NAME/KEY: CDS
<222> LOCATION: (16)..(1098)
<223> OTHER INFORMATION:

<400> SEQUENCE: 7

| gccgcgaact gcatc | atg | gag | aat | ttt | gta | gcc | acc | ttg | gct | aat | ggg | atg | 51 |
|---|---|---|---|---|---|---|---|---|---|---|---|---|---|
| | Met | Glu | Asn | Phe | Val | Ala | Thr | Leu | Ala | Asn | Gly | Met | |
| | 1 | | | | 5 | | | | | 10 | | | |

| agc | ctc | cag | ccg | cct | ctt | gaa | gaa | gtg | tcc | tgt | ggc | cag | gcg | gaa | agc | 99 |
|---|---|---|---|---|---|---|---|---|---|---|---|---|---|---|---|---|
| Ser | Leu | Gln | Pro | Pro | Leu | Glu | Glu | Val | Ser | Cys | Gly | Gln | Ala | Glu | Ser | |
| | 15 | | | | | 20 | | | | | 25 | | | | | |

| agt | gag | aag | ccc | aac | gct | gag | gac | atg | aca | tcc | aaa | gat | tac | tac | ttt | 147 |
|---|---|---|---|---|---|---|---|---|---|---|---|---|---|---|---|---|
| Ser | Glu | Lys | Pro | Asn | Ala | Glu | Asp | Met | Thr | Ser | Lys | Asp | Tyr | Tyr | Phe | |
| 30 | | | | | 35 | | | | | 40 | | | | | | |

| gac | tcc | tac | gca | cac | ttt | ggc | atc | cac | gag | gag | atg | ctg | aag | gac | gag | 195 |
|---|---|---|---|---|---|---|---|---|---|---|---|---|---|---|---|---|
| Asp | Ser | Tyr | Ala | His | Phe | Gly | Ile | His | Glu | Glu | Met | Leu | Lys | Asp | Glu | |
| 45 | | | | 50 | | | | | 55 | | | | | 60 | | |

| gtg | cgc | acc | ctc | act | tac | cgc | aac | tcc | atg | ttt | cat | aac | cgg | cac | ctc | 243 |
|---|---|---|---|---|---|---|---|---|---|---|---|---|---|---|---|---|
| Val | Arg | Thr | Leu | Thr | Tyr | Arg | Asn | Ser | Met | Phe | His | Asn | Arg | His | Leu | |
| | | | | 65 | | | | | 70 | | | | | 75 | | |

| ttc | aag | gac | aag | gtg | gtg | ctg | gac | gtc | ggc | tcg | ggc | acc | ggc | atc | ctc | 291 |
|---|---|---|---|---|---|---|---|---|---|---|---|---|---|---|---|---|
| Phe | Lys | Asp | Lys | Val | Val | Leu | Asp | Val | Gly | Ser | Gly | Thr | Gly | Ile | Leu | |
| | | 80 | | | | | 85 | | | | | 90 | | | | |

| tgc | atg | ttt | gct | gcc | aag | gcc | ggg | gcc | cgc | aag | gtc | atc | ggg | atc | gag | 339 |
|---|---|---|---|---|---|---|---|---|---|---|---|---|---|---|---|---|
| Cys | Met | Phe | Ala | Ala | Lys | Ala | Gly | Ala | Arg | Lys | Val | Ile | Gly | Ile | Glu | |
| | | 95 | | | | | 100 | | | | | 105 | | | | |

| tgt | tcc | agt | atc | tct | gat | tat | gcg | gtg | aag | atc | gtc | aaa | gcc | aac | aag | 387 |
|---|---|---|---|---|---|---|---|---|---|---|---|---|---|---|---|---|
| Cys | Ser | Ser | Ile | Ser | Asp | Tyr | Ala | Val | Lys | Ile | Val | Lys | Ala | Asn | Lys | |
| | 110 | | | | | 115 | | | | | 120 | | | | | |

| tta | gac | cac | gtg | gtg | acc | atc | atc | aag | ggg | aag | gtg | gag | gag | gtg | gag | 435 |
|---|---|---|---|---|---|---|---|---|---|---|---|---|---|---|---|---|
| Leu | Asp | His | Val | Val | Thr | Ile | Ile | Lys | Gly | Lys | Val | Glu | Glu | Val | Glu | |
| 125 | | | | 130 | | | | | 135 | | | | | 140 | | |

| ctc | cca | gtg | gag | aag | gtg | gac | atc | atc | atc | agc | gag | tgg | atg | ggc | tac | 483 |
|---|---|---|---|---|---|---|---|---|---|---|---|---|---|---|---|---|
| Leu | Pro | Val | Glu | Lys | Val | Asp | Ile | Ile | Ile | Ser | Glu | Trp | Met | Gly | Tyr | |
| | | | | 145 | | | | | 150 | | | | | 155 | | |

| tgc | ctc | ttc | tac | gag | tcc | atg | ctc | aac | acc | gtg | ctc | tat | gcc | cgg | gac | 531 |
|---|---|---|---|---|---|---|---|---|---|---|---|---|---|---|---|---|
| Cys | Leu | Phe | Tyr | Glu | Ser | Met | Leu | Asn | Thr | Val | Leu | Tyr | Ala | Arg | Asp | |
| | | | 160 | | | | | 165 | | | | | 170 | | | |

| aag | tgg | ctg | gcg | ccc | gat | ggc | ctc | atc | ttc | cca | gac | cgg | gcc | acg | ctg | 579 |
|---|---|---|---|---|---|---|---|---|---|---|---|---|---|---|---|---|
| Lys | Trp | Leu | Ala | Pro | Asp | Gly | Leu | Ile | Phe | Pro | Asp | Arg | Ala | Thr | Leu | |
| | | 175 | | | | | 180 | | | | | 185 | | | | |

| tat | gtg | acg | gcc | atc | gag | gac | cgc | cag | tac | aaa | gac | tac | aag | atc | cac | 627 |
|---|---|---|---|---|---|---|---|---|---|---|---|---|---|---|---|---|
| Tyr | Val | Thr | Ala | Ile | Glu | Asp | Arg | Gln | Tyr | Lys | Asp | Tyr | Lys | Ile | His | |
| | 190 | | | | | 195 | | | | | 200 | | | | | |

| tgg | tgg | gag | aac | gtg | tat | ggc | ttc | gac | atg | tct | tgc | atc | aaa | gat | gtg | 675 |
|---|---|---|---|---|---|---|---|---|---|---|---|---|---|---|---|---|
| Trp | Trp | Glu | Asn | Val | Tyr | Gly | Phe | Asp | Met | Ser | Cys | Ile | Lys | Asp | Val | |
| 205 | | | | 210 | | | | | 215 | | | | | 220 | | |

| gcc | att | aag | gag | ccc | cta | gtg | gat | gtc | gtg | gac | ccc | aaa | cag | ctg | gtc | 723 |
|---|---|---|---|---|---|---|---|---|---|---|---|---|---|---|---|---|
| Ala | Ile | Lys | Glu | Pro | Leu | Val | Asp | Val | Val | Asp | Pro | Lys | Gln | Leu | Val | |
| | | | | 225 | | | | | 230 | | | | | 235 | | |

| acc | aac | gcc | tgc | ctc | ata | aag | gag | gtg | gac | atc | tat | acc | gtc | aag | gtg | 771 |
|---|---|---|---|---|---|---|---|---|---|---|---|---|---|---|---|---|
| Thr | Asn | Ala | Cys | Leu | Ile | Lys | Glu | Val | Asp | Ile | Tyr | Thr | Val | Lys | Val | |
| | | | 240 | | | | | 245 | | | | | 250 | | | |

| gaa | gac | ctg | acc | ttc | acc | tcc | ccg | ttc | tgc | ctg | caa | gtg | aag | cgg | aat | 819 |
|---|---|---|---|---|---|---|---|---|---|---|---|---|---|---|---|---|
| Glu | Asp | Leu | Thr | Phe | Thr | Ser | Pro | Phe | Cys | Leu | Gln | Val | Lys | Arg | Asn | |
| | | 255 | | | | | 260 | | | | | 265 | | | | |

| gac | tac | gtg | cac | gcc | ctg | gtg | gcc | tac | ttc | aac | atc | gag | ttc | aca | cgc | 867 |

-continued

```
Asp Tyr Val His Ala Leu Val Ala Tyr Phe Asn Ile Glu Phe Thr Arg
    270                 275                 280 tgc cac aag agg acc ggc ttc tcc acc agc ccc gag tcc ccg tac acg      915
Cys His Lys Arg Thr Gly Phe Ser Thr Ser Pro Glu Ser Pro Tyr Thr
285                 290                 295                 300 cac tgg aag cag acg gtg ttc tac atg gag gac tac ctg acc gtg aag      963
His Trp Lys Gln Thr Val Phe Tyr Met Glu Asp Tyr Leu Thr Val Lys
                305                 310                 315 acg ggc gag gag atc ttc ggc acc atc ggc atg cgg ccc aac gcc aag      1011
Thr Gly Glu Glu Ile Phe Gly Thr Ile Gly Met Arg Pro Asn Ala Lys
            320                 325                 330 aac aac cgg gac ctg gac ttc acc atc gac ctg gac ttc aag ggc cag      1059
Asn Asn Arg Asp Leu Asp Phe Thr Ile Asp Leu Asp Phe Lys Gly Gln
        335                 340                 345 ctg tgc gag ctg tcc tgc tcc acc gac tac cgg atg cgc tgaggcccgg       1108
Leu Cys Glu Leu Ser Cys Ser Thr Asp Tyr Arg Met Arg
    350                 355                 360 ctctcccgcc ctgcacgagc ccaggggctg agcgttccta ggcggtttcg gggctccccc    1168
ttcctctccc tccctcccgc agaagggggt tttaggggcc tgggctgggg ggatggggag    1228
ggcacattgg gactgtgttt ttcataaatt atgtttttat atggttgcat ttaatgccaa    1288
taaatcctca gctggggaaa                                                1308

<210> SEQ ID NO 8
<211> LENGTH: 361
<212> TYPE: PRT
<213> ORGANISM: Homo sapiens

<400> SEQUENCE: 8

Met Glu Asn Phe Val Ala Thr Leu Ala Asn Gly Met Ser Leu Gln Pro
1               5                   10                  15

Pro Leu Glu Glu Val Ser Cys Gly Gln Ala Glu Ser Ser Glu Lys Pro
            20                  25                  30

Asn Ala Glu Asp Met Thr Ser Lys Asp Tyr Tyr Phe Asp Ser Tyr Ala
        35                  40                  45

His Phe Gly Ile His Glu Glu Met Leu Lys Asp Glu Val Arg Thr Leu
    50                  55                  60

Thr Tyr Arg Asn Ser Met Phe His Asn Arg His Leu Phe Lys Asp Lys
65                  70                  75                  80

Val Val Leu Asp Val Gly Ser Gly Thr Gly Ile Leu Cys Met Phe Ala
                85                  90                  95

Ala Lys Ala Gly Ala Arg Lys Val Ile Gly Ile Glu Cys Ser Ser Ile
            100                 105                 110

Ser Asp Tyr Ala Val Lys Ile Val Lys Ala Asn Lys Leu Asp His Val
        115                 120                 125

Val Thr Ile Ile Lys Gly Lys Val Glu Glu Val Glu Leu Pro Val Glu
    130                 135                 140

Lys Val Asp Ile Ile Ile Ser Glu Trp Met Gly Tyr Cys Leu Phe Tyr
145                 150                 155                 160

Glu Ser Met Leu Asn Thr Val Leu Tyr Ala Arg Asp Lys Trp Leu Ala
                165                 170                 175

Pro Asp Gly Leu Ile Phe Pro Asp Arg Ala Thr Leu Tyr Val Thr Ala
            180                 185                 190

Ile Glu Asp Arg Gln Tyr Lys Asp Tyr Lys Ile His Trp Trp Glu Asn
        195                 200                 205

Val Tyr Gly Phe Asp Met Ser Cys Ile Lys Asp Val Ala Ile Lys Glu
```

```
                   210                 215                 220
Pro Leu Val Asp Val Val Asp Pro Lys Gln Leu Val Thr Asn Ala Cys
225                 230                 235                 240

Leu Ile Lys Glu Val Asp Ile Tyr Thr Val Lys Val Glu Asp Leu Thr
                245                 250                 255

Phe Thr Ser Pro Phe Cys Leu Gln Val Lys Arg Asn Asp Tyr Val His
                260                 265                 270

Ala Leu Val Ala Tyr Phe Asn Ile Glu Phe Thr Arg Cys His Lys Arg
                275                 280                 285

Thr Gly Phe Ser Thr Ser Pro Glu Ser Pro Tyr Thr His Trp Lys Gln
                290                 295                 300

Thr Val Phe Tyr Met Glu Asp Tyr Leu Thr Val Lys Thr Gly Glu Glu
305                 310                 315                 320

Ile Phe Gly Thr Ile Gly Met Arg Pro Asn Ala Lys Asn Asn Arg Asp
                325                 330                 335

Leu Asp Phe Thr Ile Asp Leu Asp Phe Lys Gly Gln Leu Cys Glu Leu
                340                 345                 350

Ser Cys Ser Thr Asp Tyr Arg Met Arg
                355                 360

<210> SEQ ID NO 9
<211> LENGTH: 353
<212> TYPE: PRT
<213> ORGANISM: Artificial Sequence
<220> FEATURE:
<223> OTHER INFORMATION: synthetic

<400> SEQUENCE: 9

Met Ala Ala Glu Ala Ala Asn Cys Ile Met Glu Val Ser Cys Gly
1               5                   10                  15

Gln Ala Glu Ser Ser Glu Lys Pro Asn Ala Glu Asp Met Thr Ser Lys
                20                  25                  30

Asp Tyr Tyr Phe Asp Ser Tyr Ala His Phe Gly Ile His Glu Glu Met
                35                  40                  45

Leu Lys Asp Glu Val Arg Thr Leu Thr Tyr Arg Asn Ser Met Phe His
50                  55                  60

Asn Arg His Leu Phe Lys Asp Lys Val Val Leu Asp Val Gly Ser Gly
65                  70                  75                  80

Thr Gly Ile Leu Cys Met Phe Ala Ala Lys Ala Gly Ala Arg Lys Val
                85                  90                  95

Ile Gly Ile Glu Cys Ser Ser Ile Ser Asp Tyr Ala Val Lys Ile Val
                100                 105                 110

Lys Ala Asn Lys Leu Asp His Val Val Thr Ile Ile Lys Gly Lys Val
                115                 120                 125

Glu Glu Val Glu Leu Pro Val Glu Lys Val Asp Ile Ile Ile Ser Glu
                130                 135                 140

Trp Met Gly Tyr Cys Leu Phe Tyr Glu Ser Met Leu Asn Thr Val Leu
145                 150                 155                 160

His Ala Arg Asp Lys Trp Leu Ala Pro Asp Gly Leu Ile Phe Pro Asp
                165                 170                 175

Arg Ala Thr Leu Tyr Val Thr Ala Ile Glu Asp Arg Gln Tyr Lys Asp
                180                 185                 190

Tyr Lys Ile His Trp Trp Glu Asn Val Tyr Gly Phe Asp Met Ser Cys
                195                 200                 205

Ile Lys Asp Val Ala Ile Lys Glu Pro Leu Val Asp Val Val Asp Pro
```

```
            210                 215                 220
Lys Gln Leu Val Thr Asn Ala Cys Leu Ile Lys Glu Val Asp Ile Tyr
225                 230                 235                 240

Thr Val Lys Val Glu Asp Leu Thr Phe Thr Ser Pro Phe Cys Leu Gln
                245                 250                 255

Val Lys Arg Asn Asp Tyr Val His Ala Leu Val Ala Tyr Phe Asn Ile
            260                 265                 270

Glu Phe Thr Arg Cys His Lys Arg Thr Gly Phe Ser Thr Ser Pro Glu
        275                 280                 285

Ser Pro Tyr Thr His Trp Lys Gln Thr Val Phe Tyr Met Glu Asp Tyr
    290                 295                 300

Leu Thr Val Lys Thr Gly Glu Glu Ile Phe Gly Thr Ile Gly Met Arg
305                 310                 315                 320

Pro Asn Ala Lys Asn Asn Arg Asp Leu Asp Phe Thr Ile Asp Leu Asp
                325                 330                 335

Phe Lys Gly Gln Leu Cys Glu Leu Ser Cys Ser Thr Asp Tyr Arg Met
            340                 345                 350

Arg

<210> SEQ ID NO 10
<211> LENGTH: 360
<212> TYPE: PRT
<213> ORGANISM: Artificial Sequence
<220> FEATURE:
<223> OTHER INFORMATION: synthetic

<400> SEQUENCE: 10

Met Glu Asn Phe Val Ala Thr Leu Ala Asn Gly Met Ser Leu Gln Pro
1               5                   10                  15

Pro Leu Glu Glu Val Ser Cys Gly Gln Ala Glu Ser Ser Glu Lys Pro
                20                  25                  30

Asn Ala Glu Asp Met Thr Ser Lys Asp Tyr Tyr Phe Asp Ser Tyr Ala
            35                  40                  45

His Phe Gly Ile His Glu Glu Met Leu Lys Asp Glu Val Arg Thr Leu
        50                  55                  60

Thr Tyr Arg Asn Ser Met Phe His Asn Arg His Leu Phe Lys Asp Lys
65                  70                  75                  80

Val Val Leu Asp Val Gly Ser Gly Thr Gly Ile Leu Cys Met Phe Ala
                85                  90                  95

Ala Lys Ala Gly Ala Arg Lys Val Ile Gly Ile Val Cys Ser Ser Ile
            100                 105                 110

Ser Asp Tyr Ala Val Lys Ile Val Lys Ala Asn Lys Leu Asp His Val
        115                 120                 125

Val Thr Ile Ile Lys Gly Lys Val Glu Glu Val Glu Leu Pro Val Glu
    130                 135                 140

Lys Val Ala Ser Ser Ala Ser Gly Trp Ala Thr Ala Ser Ser Thr
145                 150                 155                 160

Ser Pro Cys Ser Thr Pro Cys Ser Met Pro Gly Thr Ser Val Ala Pro
                165                 170                 175

Asp Gly Leu Ile Phe Pro Asp Arg Ala Thr Leu Tyr Val Thr Ala Ile
            180                 185                 190

Glu Asp Arg Gln Tyr Lys Asp Tyr Lys Ile His Trp Trp Glu Asn Val
        195                 200                 205

Tyr Gly Phe Asp Met Ser Cys Ile Lys Asp Val Ala Ile Lys Glu Pro
    210                 215                 220
```

```
Leu Val Asp Val Val Asp Pro Lys Gln Leu Val Thr Asn Ala Cys Leu
225                 230                 235                 240

Ile Lys Glu Val Asp Ile Tyr Thr Val Lys Val Glu Asp Leu Thr Phe
            245                 250                 255

Thr Ser Pro Phe Cys Leu Gln Val Lys Arg Asn Asp Tyr Val His Ala
        260                 265                 270

Leu Val Ala Tyr Phe Asn Ile Glu Phe Thr Arg Cys His Lys Arg Thr
    275                 280                 285

Gly Phe Ser Thr Ser Pro Glu Ser Pro Tyr Thr His Trp Lys Gln Thr
290                 295                 300

Val Phe Tyr Met Glu Asp Tyr Leu Thr Val Lys Thr Gly Glu Glu Ile
305                 310                 315                 320

Phe Gly Thr Ile Gly Met Arg Pro Asn Ala Lys Asn Asn Arg Asp Leu
            325                 330                 335

Asp Phe Thr Ile Asp Leu Asp Phe Lys Gly Gln Leu Cys Glu Leu Ser
        340                 345                 350

Cys Ser Thr Asp Tyr Arg Met Arg
        355                 360

<210> SEQ ID NO 11
<211> LENGTH: 10
<212> TYPE: PRT
<213> ORGANISM: Artificial Sequence
<220> FEATURE:
<223> OTHER INFORMATION: synthetic

<400> SEQUENCE: 11

Gly Gly Phe Gly Gly Arg Gly Gly Phe Gly
1               5                   10

<210> SEQ ID NO 12
<211> LENGTH: 22
<212> TYPE: DNA
<213> ORGANISM: Artificial Sequence
<220> FEATURE:
<223> OTHER INFORMATION: synthetic

<400> SEQUENCE: 12
ggctacaaaa ttctccatga tg                                              22

<210> SEQ ID NO 13
<211> LENGTH: 21
<212> TYPE: DNA
<213> ORGANISM: Artificial Sequence
<220> FEATURE:
<223> OTHER INFORMATION: synthetic

<400> SEQUENCE: 13
tggccgtcac atacagcgtg g                                               21
```

IFN RECEPTOR 1 BINDING PROTEINS, DNA ENCODING THEM, AND METHODS OF MODULATING CELLULAR RESPONSE TO INTERFERONS

CROSS-REFERENCE TO RELATED APPLICATIONS

The present application is a continuation of U.S. application Ser. No. 09/341,640, filed Oct. 8, 1999, now abandoned, which is the national stage under 35 U.S.C. 371 of PCT/US98/00671, filed Jan. 15, 1998, which international application claims the benefit under 35 U.S.C. §119(e) of U.S. provisional application No. 60/035,636, filed Jan. 15, 1997, now abandoned.

FIELD OF THE INVENTION

The present invention relates generally to the molecular mechanisms of interferon action and, more specifically, to novel interferon receptor 1-binding proteins, recombinant DNA molecules encoding them, and methods for modulating cellular response to interferon.

BACKGROUND OF THE INVENTION

Type I interferons (IFN-α and -β subtypes) produce pleiotropic effects on cells, such as inhibition of virus replication (antiviral effect), inhibition of cell proliferation (anti-tumoral effects), and modulation of immune cell activities (immunoregulatory effects). These multiple effects of interferons (IFNs) are correlated with morphological and biochemical modifications of cells (Revel, 1984, for review).

Interferons exert their activities through species-specific receptors. For type I IFNs, two transmembranal receptor chains have been identified: IFNAR1 (Uze et al, 1990) and IFNAR2-2 (or IFNAR2-c, Domanski et al, 1995). Transduction of the signal generated by IFN-α, β, ω involves protein tyrosine kinases of the Janus kinases (Jak) family and transcription factors of the Stat family (Darnell et al, 1994). Proteins of the Jak-Stat pathways are activated by binding to the intracytoplasmic (IC) domains of the IFNAR1 and IFNAR2 receptor chains. Among the proteins binding to the IFNAR1 IC domain are tyk2 and Stat2 (Abramovich et al, 1994). Stat2 would then recruit Stat1 to form the IFN-induced ISGF3 transcription complex which activates IFN-induced genes (Leung et al, 1995). Transcription complexes containing Stat3 are also induced by IFN-β (Harroch et al, 1994) and an IFN-dependent binding of Stat3 to IFNAR1-IC was observed (Yang et al, 1996). Protein-tyrosine phosphatase PTP1C and D reversibly associate with IFNAR1 upon IFN addition (David et al, 1995a). In addition, two serine/threonine protein kinases, the 48 kDa ERK2 MAP kinase (David et al, 1995b) and the cAMP activated protein kinase A (David et al, 1996) bind to the isolated membrane-proximal 50 residues of IFNAR1-IC. Therefore, the type I IFN receptor IC domains serve as docking sites for multiple proteins which serve to generate and regulate the biological effects of IFNs on cells.

Two-hybrid screening in yeast is a potent method for identifying new proteins which bind to defined polypeptide sequences (Fields and Song, 1989). Briefly, the two-hybrid screen is performed by transfecting yeast cells with (a) a plasmid DNA in which the defined polypeptide (bait) is fused to the DNA-binding domain of the Gal4 transcription factor, and (b) a cDNA library fused to the activation domain of Gal4 in a pACT plasmid. Yeast cells transfected with a cDNA that encodes for a protein which binds to the polypeptide bait will then reconstitute the Gal4 activity. The presence of such a protein which binds the polypeptide bait is revealed by expression of an enzymatic activity, such as β-galactosidase, from a GAL1-lacZ construct that is preferably introduced into the yeast genome. From yeast clones which are positive in this test, it is possible to isolate the pACT plasmid, to determine the nucleotide sequence of its insert and to identify the protein which it encodes. This method has allowed the identification of novel proteins which interact with the IC domain of cytokine receptors (Boldin et al, 1995).

Citation of any document herein is not intended as an admission that such document is pertinent prior art, or considered material to the patentability of any claim of the present application. Any statement as to content or a date of any document is based on the information available to applicants at the time of filing and does not constitute an admission as to the correctness of such a statement.

SUMMARY OF THE INVENTION

The present invention relates to two novel human proteins, herein designated IR1B1 and IR1B4, which have been identified to be IFN Receptor 1 (IFNAR1) binding proteins, and to the DNA encoding these two proteins. Each of IR1B1 and IR1B4 proteins interacts with the intracytoplasmic (IC) domain of IFNAR1 and mediates the cellular responses to interferon.

The present invention is directed to a recombinant DNA molecule containing a nucleotide sequence encoding either the IR1B1 or IR1B4 proteins, or fragments thereof, as well as the proteins encoded thereby. In the recombinant DNA molecules, the nucleotide sequence encoding the IR1B1 or IR1B4 protein, or fragments thereof, is operably linked to a promoter in either a sense orientation or an anti-sense orientation.

By administering the recombinant DNA molecule containing a promoter operably linked to the nucleotide sequence encoding a novel IFNAR1 binding protein in the sense orientation directly into tumors, the response to exogenous interferon therapy in the treatment of cancer is enhanced.

Furthermore, the present invention also relates to a method of prolonging tissue graft survival by introducing the recombinant molecule containing a promoter operably-linked to the nucleotide sequence encoding a novel IFNAR1 binding protein, or fragment thereof, in the anti-sense orientation into the graft tissue prior to grafting to the patient.

Thus, the present invention also relates to pharmaceutical compositions containing such DNA, RNA or protein and therapeutic methods for using same.

The present invention also relates to antibodies specific to the novel proteins of the present invention.

BRIEF DESCRIPTION OF THE DRAWINGS

FIG. 2 shows the interaction of IR1B4 with the IFNAR1-IC domain as measured by the two-hybrid genetic interaction analysis in yeast. In the boxed lower portion of the figure, the cDNA insert in pACT as combined with various "baits" are indicated.

FIG. 3 shows the nucleotide (SEQ ID NO:1) and amino acid (SEQ ID NO: 2) sequence of IR1E1.

FIG. 4 shows the homology and alignment of the amino acid sequence of IR1B1 (SEQ ID NO:2) with the amino acid sequences of two calcium-binding proteins, calcineurin B (abbreviated CALB; SEQ ID NO:3) and caltractin (abbreviated CATR; SEQ ID NO:4). Identical amino acids in IR1B1 and CALB or between CALB and CATR are shown by the symbol "|" therebetween. Identity between IR1B1 and CATR, but not with CALB, is shown by the symbol ":" therebetween. Regions shown in bold type are the calcium binding helix-loop-helix EF-hand domains.

In FIG. 6A, the [$^{35}$S]methionine-labeled translation products with or without flag-IR1B4 in vitro transcripts were either immunoprecipitated (10 µl) with anti-flag M2 beads (lanes 1 and 4), or reacted (50 µl) with glutathione beads coupled to GST fused to the 100 amino acid long IFNAR1-IC domain (lanes 2 and 5) or coupled to GST alone (lanes 3 and 6). After overnight incubation at 4° C. (final volume 100 µl), the beads were washed and SDS-eluted proteins boiled in reducing conditions before SDS-PAGE. In FIG. 6B, U266S (lane 1) or U266R cells (lane 2) were extracted with Brij buffer and antiproteases (Abramovich et al, 1994) and 0.35 ml ($10^7$ cells) was incubated with 75 µl of [$^{35}$S]methionine-labeled translation products of flag-IR1B4 transcripts overnight at 4° C. Anti-IFNAR1 mAb R3 immobilized on protein G beads (25 µl) was added for 2.5 hr, washed in Brij buffer, and SDS-eluted, boiled and reduced proteins analyzed by SDS-PAGE. A control with anti-flag M2 beads as above was run (lane 3). The dried gels were visualized in a Phosphor-Imager. In the first three lanes of FIG. 6A, no IR1B4 mRNA was added to the in vitro translation reaction. In the second three lanes of FIG. 6A, mRNA encoding IR1B4 protein fused to the flag protein was translated in an in vitro system.

FIG. 7 shows the nucleotide (SEQ ID NO:7) and deduced amino acid sequence (SEQ ID NO:8) of IR1B4.

FIG. 8 shows the amino acid alignment of IR1B4 (SEQ ID NO:8) and PRMT1 (SEQ ID NO:9) and their differences.

FIG. 9 shows the amino acid alignment of IR1B4 and HCP-1 (SEQ ID NO:10) and their differences.

DETAILED DESCRIPTION OF THE INVENTION

Figure 1:
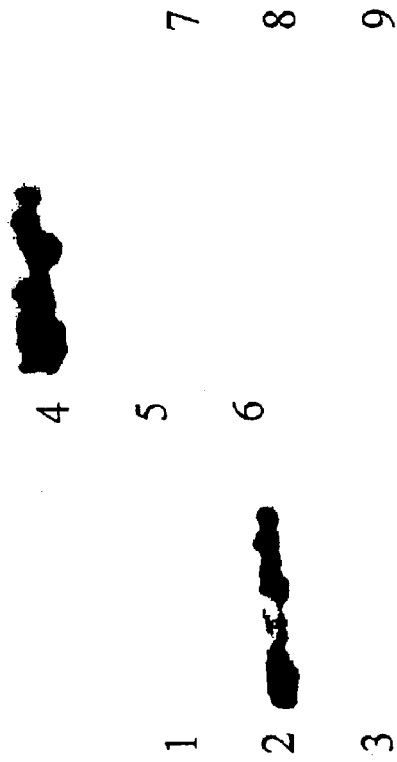
FIG. 1 shows the interaction of IR1B1 with the IFNAR1-IC domain as measured by the two-hybrid genetic interaction analysis in yeast. In the boxed lower portion of the figure, the cDNA insert in pACT as combined with various "baits" are indicated.

The present invention relates to the discovery of two novel human proteins which interact with the intracytoplasmic domain (IC) of the IFNAR1 chain of the interferon type 1 (IFN-α, β or ω) receptor and are designated herein as IFN Receptor Binding protein 1 (IR1B1) and IFN Receptor Binding Protein 4 (IR1B4). The interaction of these two novel proteins with IFNAR1 was demonstrated with a two-hybrid genetic test in yeast where transfection of the yeast reporter strain SFY526 (Bartel et al, 1993) with IR1B1 or IR1B4 cDNA fused to the Gal4 activation domain resulted in β-galactosidase activity only when the IFNAR1-IC domain (fused to the Gal4 DNA-binding domain) was used as bait.

The sequence of IR1B1 cDNA encodes a 191 amino acid polypeptide. Computer searches of sequence databases revealed that IR1B1 is a novel protein which shows marked homology, e.g., calcium binding sites (E-F handles), to the calcium binding proteins, calcineurin P and caltractin. Calcineurin P (Guerini et al, 1989) is a 19 kDa subunit of a serine/threonine phosphatase which plays a key role in activating the translocation of transcription factor NFAT to the nucleus of T-lymphocytes, and which is inhibited by immunosuppressive drugs such as cyclosporin. Caltractin (Lee and Huang, 1993), a 21 kDa protein, is a cytoskeleton-associated protein found in centrosomes, and is involved in the movement of chromosomes during mitosis, and more generally in microtubule organization centers. Thus, the novel IR1B1 protein is a new member of the calcineurin and caltractin family of calcium-regulated proteins.

The gene for IR1B1 was surprisingly found to be rapidly activated in human cells by IFN treatment. Thus, this is the first example of a calcium-binding protein which is induced by IFN. Since calcium ions regulate cell morphology, adhesion and division, modulation of IR1B1 activity in cells could affect the response of normal and malignant cells to IFN. The role of IR1B1 in mediating the action of IFN in cells is supported by the interaction of IR1B1 with the IC-domain of an IFN receptor chain.

While IR1B4, like IR1B1, was found to be a novel protein as determined by computer searches of sequence databases, it was also found that IR1B4 has sequence homology to enzymes which utilize S-adenosyl methionine for methylating arginine residues in proteins and are designated as protein arginine methyltransferases (PRMT1; Kagan and Clarke, 1994; Lin et al, 1996). IR1B4 was found to bind directly to the IC-domain of IFNAR1 in vitro, and the constitutive association of PRMT activity with the IFNAR chain of the IFN-α, β receptor isolated from human cells was demonstrated by methylation of histones. When antisense oligodeoxynucleotides from the IR1B4 cDNA was added to human cell cultures, depletion of PRMT activity in the cell culture was observed. Human myeloma cells that were treated in this manner showed a much reduced response to IFN as measured by growth-inhibition. Therefore, IR1B4/PRMT is involved in the pathway by which the IFN receptor causes growth-inhibition in tumor cells and is also involved in other functions of the IFN receptor. Known substrates of PRMT include a number of RNA and DNA binding proteins, and in particular heterologous nuclear ribonucleoproteins (hnRNPs). The hnRNPs are involved in mRNA transport from the nucleus to the cytoplasm, alternative splicing of pre-mRNA, and post-transcriptional controls (Liu and Dreyfuss, 1995). Accordingly, the novel human IR1B4/PRMT cDNA and protein, which were discovered by its association with the IFN receptor, can be used to modify the response of human or animal cells to IFN.

A recombinant DNA molecule according to the present invention contains a nucleotide sequence that encodes the IR1B or IR1B4 protein, or a fragment thereof, and can be used either to increase the cellular response to IFN by increasing expression of IR1B1 or IR1B4 cDNA or to decrease the cellular response to IFN by decreasing the expression of IR1B1 or IR1B4 proteins with anti-sense RNA molecules.

The increased in vivo expression of IR1B1 or IR1B4 cDNA would be useful in cancer therapy where the increased cellular response to IFN would result in a decrease in malignant cell growth and an enhanced response to exogenous IFN therapy. To obtain increased in vivo expression of IR1B1 and IR1B4 at the target location for increased cellular response to IFN, expression vectors containing IR1B1 or IR1B4 cDNA operably-linked in a sense orientation to a strong constitutive promoter can be injected directly at the target location, such as into brain tumors or metastatic tumor nodules (e.g., melanoma or breast cancer).

Conversely, the decreased in vivo expression of IR1B1 or IR1B4 proteins would be useful in prolonging the survival of tissue grafts as the rejection of these grafts in the host is mediated by the histocompatibility antigens (MHC class I) whose synthesis depends on the IFN stimulus. When the cDNA of, IR1B1 or IR1B4, or fragments thereof, carried on a suitable vector and operably-linked in an anti-sense orientation to a promoter, is introduced into cells of the tissue to be grafted, the expression of anti-sense RNA leads to the degradation of IR1B1 or IR1B4 mRNA (or sense RNA for IR1B1/IR1B4) and a consequent decrease in the cellular levels of IR1B1 or IR1B4 protein.

Anti-sense RNA is transcribed from an upstream promoter operably-linked to a coding sequence oriented in the anti-sense direction, i.e., opposite the normal or sense direction of the DNA and its transcribed sense RNA (mRNA). The expression of anti-sense RNA complementary to the sense RNA is a powerful way of regulating the biological function of RNA molecules. Through the formation of a stable duplex between sense RNA and anti-sense RNA, the normal or sense RNA transcript is rendered inactive and untranslatable.

Recombinant DNA molecules, as embodiments of the present invention, contain the cDNA of IR1B1 or IR1B4, or fragments thereof, operably-linked to a promoter in either a sense or anti-sense orientation. The term "promoter" is meant to comprehend a double-stranded DNA or RNA sequence which is capable of binding RNA polymerase and promoting the transcription of an "operably linked" nucleic acid sequence. Thus, a DNA sequence would be operably linked to a promoter sequence if the promoter is capable of effecting the transcription of the DNA sequence, regardless of the orientation of the DNA sequence.

The types of promoters used to control transcription may be any of those which are functional in the host/target cells. Examples of promoters functional in mammalian cells include the SV40 early promoter, adenovirus major late promoter, herpes simplex (HSV) thymidine kinase promoter, rous sarcoma (RSV) LTR promoter, human cytomegalovirus (CMV) immediate early promoter, mouse mammary tumor virus (MMTV) LTR promoter, interferon β promoter, heat shock protein 70 (hsp70) promoter, as well as many others well known in the art.

A promoter operably linked to IR1B1 or IR1B4 cDNA in the sense orientation for expression of IR1B1 or IR1B4 protein is preferably a strong constitutive promoter. This allows for a high level of IR1B1 or IR1B4 regardless of the presence of endogenous cellular mechanisms for regulating the expression of IR1B1 or IR1B4.

Likewise, the promoter, which is operably linked to IR1B1 or IR1B4 cDNA in the anti-sense orientation, is preferably a strong promoter, such as the promoter present in the Epstein-Barr Virus (EBV) regulating region which allows for high levels of anti-sense RNA expression (Deiss and Kimchi, 1991).

The anti-sense sequence is preferably only expressible in the host/target cells, which are preferably human cells and the expressed anti-sense RNA should be stable (i.e., does not undergo rapid degradation). The anti-sense RNA should only specifically hybridize to the sense mRNA expressed in host/target cells, and form a stable double-stranded RNA molecule that is essentially non-translatable. In other words, the anti-sense RNA expressed in host/target cells prevents the expressed sense mRNA from being translated into IR1B1 or IR1B4 proteins. The vector-borne anti-sense sequence may carry either the entire IR1B1 or IR1B4 cDNA sequence or merely a portion thereof, as long as the anti-sense portion is capable of hybridizing to sense mRNA and preventing its translation into IR1B1 or IR1B4 protein. Accordingly, an "anti-sense" sequence as used throughout the specification and claims is defined as the entire anti-sense sequence or a portion thereof which is capable of being expressed in transformed/transfected cells, and which is also capable of specifically hybridizing to "sense" IR1B1 or IR1B4 mRNA to form a non-translatable double-stranded RNA molecule.

The anti-sense sequence need not hybridize to the entire length of the IR1B1 or IR1B4 mRNA. Instead, it may hybridize to selected regions, such as the 5'-untranslated non-coding sequence, the coding sequence, or the 3'-untranslated sequence of the "sense" mRNA. Preferably, the anti-sense sequence hybridizes to the 5'-coding sequence and/or 5'-non-coding region, such as at cap and initiation codon sites, since it has been observed it has been observed with many examples of anti-sense oligonucleotides that targeting the initiation codon is more effective, whereas targeting internal sequences within the coding region is not as effective (Wickstrom, 1991). The effectiveness of an anti-sense sequence in preventing translation of IR1B4 sense mRNA can easily be tested in an assay for protein-arginine methyltransferase activity in U266S cells as described in Example 7. In view of the size of the mammalian genome, the anti-sense IR1B1 or IR1B4 sequence is preferably at least 17, more preferably at least 30 base pairs in length. However, shorter sequences may still be useful, i.e., they either fortuitously do not hybridize to other mammalian sequences, or such "cross-hybridization" does not interfere with the metabolism of the cell in a manner and to a degree which prevents the accomplishment of the objects of this invention.

Both the preferred hybridization target and the preferred anti-sense sequence length are readily determined by systematic experiment. Standard methods such as described in Ausubel et al, eds. *Current Protocols in Molecular Biology*, Greene Publishing Assoc., New York, N.Y., 1987–1996, and Sambrook et al, *Molecular Cloning: A Laboratory Manual*, Second Edition, Cold Spring Harbor Press, Cold Spring Harbor, N.Y. (1989) can be used to systematically remove an increasingly larger portion of the anti-sense sequence from the vector. Besides the full length anti-sense sequence, a series of staggered deletions may be generated, preferably at the 5'-end of the anti-sense sequence. This creates a set of truncated anti-sense sequences that still remain complementary to preferably the 5'-end of the sense mRNA and as a result, still forms an RNA molecule that is double-stranded at the 5'-end of the sense mRNA (complements the 3'-end of an anti-sense RNA) and remains non-translatable. Moreover, anti-sense oligonucleotides, such as oligonucleotide AS-1 (SEQ ID NO:12), can be readily synthesized chemically and introduced onto a vector in operable linkage with a promoter for use in decreasing the in vivo cellular expression of IR1B1 or IR1B4 protein.

The vectors of the present invention may be any suitable eukaryotic or prokaryotic vector normally used for transfecting mammalian cells, such as episomal, replicable, or chromosomally integratable vectors well-known in the art. A particularly preferred vector for the expression of IR1B1 or IR1B4 anti-sense RNA is the episomal plasmid containing the Epstein-Barr Virus regulatory region (Deiss and Kimchi, 1991) to serve as the promoter that is operably-linked to IR1B1 or IR1B4 cDNA arranged in an anti-sense orientation relative to this regulatory region. The use of anti-sense vectors and oligonucleotide phosphorothioates are addressed in *Annals of the New York of Sciences: Gene Therapy for Neoplastic Diseases*. eds. B. E. Huber and J. S. Lazo, Vol. 716, 1994 (e.g. Milligan et al, pp. 228–241).

According to the present invention, the survival of tissues or organs grafted to a patient in need of such a graft can be prolonged by decreasing the cellular response to IFN. Rejection of graft tissue is mediated by the histocompatibility antigens, with the synthesis of these MHC class I antigens being dependent on IFN stimulus. Thus, a decrease in cellular response to IFN stimulus will prolong the survival of graft tissue. The method for prolonging tissue graft survival according to the present invention involves introducing into cells of a tissue or organ to be grafted to a patient a recombinant DNA molecule containing a IR1B1 or IR1B4 cDNA sequence, or fragment thereof, operably linked to a promoter in the anti-sense orientation, whereby anti-sense IR1B1 or IR1B4 RNA is expressed in such transfected/transformed cells. The recombinant DNA molecule can be introduced into the cells of a tissue or organ in any manner well-known in the art to be suitable for this purpose. Following the introduction of the recombinant DNA molecule into cells of the tissue or organ, the tissue or organ can be grafted to the patient in need of such a graft.

A pharmaceutical composition containing a recombinant DNA molecule, which is an expression vector and which carries IR1B1 or IR1B4 cDNA operably linked to a promoter in a sense orientation, can be injected directly into tumors, e.g., brain tumors and metastatic tumor nodules, to make the cells within these tumors more responsive to exogenous IFN therapy as a treatment for cancer. The enhanced cellular response to exogenous IFN therapy would lead to an inhibition of malignant cell growth.

Gene transfer in vivo or ex vivo is well-reported, i.e., in *Annals of the New York Academy of Sciences: Gene Therapy for Neoplastic Diseases*, Vol. 716, 1994; see, for example, "Direct Gene Transfer for the Understanding and Treatment of Human Disease" by G. E. Plautz on pages 144–153, and "Mechanisms of Action of the p53 Tumor suppressor and Prospects for Cancer Gene Therapy by Reconstitution of p53 Function" by Roemer et al, on pages 265–282. Methods of inserting recombinant DNA molecules into cells of a tissue or organ to be grafted or of a tumor include adenovirus, retrovirus, adenovirus-associated virus (AAV) vectors, as well as direct DNA injection or oligonucleotide-liposome injection. Clinical trials where retroviral vectors are injected into brain tumors or where adenovirus is used to infect upper respiratory tract cells of a patient with cystic fibrosis are well-known.

Pharmaceutical compositions comprising the recombinant DNA molecule encoding IR1B1 or IR1B4 cDNA, or a fragment thereof, either in a sense or anti-sense orientation with respect to an operably linked promoter, is intended to include all compositions where the recombinant DNA molecule is contained in an amount effective for achieving its intended purpose. In addition, the pharmaceutical compositions may contain suitable pharmaceutically acceptable carriers or excipients which stabilize the recombinant DNA molecule or facilitate its administration.

Another embodiment of the present invention is directed to molecules which include the antigen-binding portion of an antibody specific for IFNAR1-binding proteins IR1B1 or IR1B4, or fragments thereof, for use in diagnostics, such as immunodetection methods to assay for the level of IR1B1 or IR1B4 proteins in tumor tissue obtained from biopsies or for use in affinity chromatography purification of the protein.

The term "antibody" is meant to include polyclonal antibodies, monoclonal antibodies (mAbs), chimeric antibodies, anti-idiotypic (anti-Id) antibodies, single-chain antibodies, and recombinantly produced humanized antibodies, as well as active fractions thereof provided by any known technique, such as, but not limited to enzymatic cleavage, peptide synthesis or recombinant techniques.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs may be obtained by methods known to those skilled in the art. See, for example Kohler and Milstein, *Nature* 256:495–497 (1975); U.S. Pat. No. 4,376,110; Ausubel et al, eds., supra, Harlow and Lane ANTIBODIES: A LABORATORY MANUAL Cold Spring Harbor Laboratory (1988); and Colligan et al, eds., CURRENT PROTOCOLS IN IMMUNOLOGY, Greene Publishing Assoc. and Wiley Interscience, N.Y., (1992, 1993), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production.

Chimeric antibodies are molecules different portions of which are derived from different animal species, such as those having the variable region derived from a murine mAb and a human immunoglobulin constant region. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al, *Proc. Natl. Acad. Sci. USA* 81:3273–3277 (1984); Morrison et al, *Proc. Natl. Acad. Sci. USA* 81:68516855 (1984); Boulianne et al, *Nature* 312:643–646 (1984); Cabilly et al, European Patent Application 125023 (published Nov. 14, 1984); Neuberger et al, *Nature* 314: 268–270 (1985); Taniguchi et al, European Patent Application 171496 (published Feb. 19, 1985); Morrison et al, European Patent Application 173494 (published Mar. 5, 1986); Neuberger et al, PCT Application WO 8601533, (published Mar. 13, 1986); Kudo et al, European Patent Application 184187 (published Jun. 11, 1986); Morrison et al, European Patent Application 173494 (published Mar. 5, 1986); Sahagan et al, *J. Immunol.* 137:1066–1074 (1986); Robinson et al, International Patent Publication, WO 9702671 (published 7 May 1987); Liu et al, *Proc. Natl. Acad. Sci. USA* 84:3439–3443 (1987); Sun et al, *Proc. Natl. Acad. Sci. USA* 84:214–218 (1987); Better et al, *Science* 240:1041–1043 (1988); and Harlow and Lane, ANTIBODIES: A LABORATORY MANUAL, supra.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

It should be understood that antibodies of the present invention may be intact antibodies, such as monoclonal antibodies, but that it is the epitope binding site of the antibody which provides the desired function. Thus, besides the intact antibody, proteolytic fragments thereof such as the Fab or F(ab')2 fragments can be used. Fab and F(ab')2 fragments lack the Fc fragment of intact antibody, clear more rapidly from the circulation, and may have less nonspecific tissue binding than an intact antibody (Wahl et al, *J. Nucl. Med.* 24:316–325 (1983)). Such fragments are typically produced by proteolytic cleavage, using enzymes such as papain (to produce Fab fragments) or pepsin (to produce F(ab')2 fragments).

Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (see Eshhar, Z. et al, *Br. J. Cancer Suppl.*, 10:27–9, 1990; Gross, G. et al, *Proc. Natl. Acad. Sci. USA*, 86:10024–8, 1989). Single chain antibodies can also be produced and used. Single chain antibodies can be single chain composite polypeptides having antigen binding capabilities and comprising a pair of amino acid sequences homologous or analogous to the variable regions of an immunoglobulin light and heavy chain (linked $V_H$-$V_L$ or single chain Fv). Both $V_H$ and $V_L$ may copy natural monoclonal antibody sequences or one or both of the chains may comprise a CDR-FR construct of the type described in U.S. Pat. No. 5,091,513. The separate polypeptides analogous to the variable regions of the light and heavy chains are held together by a polypeptide linker. Methods of production of such single antibodies, particularly where the DNA encoding the polypeptide structures of the $V_H$ and $V_L$ chains are known, may be accomplished in accordance with the methods described, for example, in U.S. Pat. No. 4,946,778, 5,091,513 and 5,096,815.

Thus, the term "a molecule which includes the antigen-binding portion of an antibody" is intended to include not only intact immunoglobulin molecules of any isotype and generated by any animal cell line or microorganism, but also the reactive fraction thereof including, but not limited to, the Fab fragment, the Fab' fragment, the F(ab')2 fragment, the variable portion of the heavy and/or light chains thereof, and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction.

Having now fully described the invention, the same will be more readily understood through reference to the following examples which are provided by way of illustration and is not intended to be limiting of the present invention.

EXAMPLE 1

Two Human Proteins, IR1B1 and IR1B4, Bind to the IFN Receptor

A cDNA fragment encoding the entire IFNAR1-IC domain amplified by PCR using a BamH1-sense primer (5'ctgaggatccAAAGTCTTCTTGAGATGCATC (SEQ ID NO:5)) and an EcoRI anti-sense primer (5'tgacgaattcctaT-CATACAAAGTC (SEQ ID NO:6)), was cloned in a Bluescript vector (BS—SK+, Stratagene). The BamHI-SalI fragment from this BS-IFNAR1-IC was introduced in the pGBT$_{10}$ vector (CloneTech) and fused in-phase after the Gal4 DNA binding domain (pGBT$_{10}$-IFNAR1-IC) for two-hybrid screening. The two-hybrid screening method (Fields and Song, 1989) was carried out with the modified procedure of Durfee et al (1993) using the pACT plasmid cDNA library from human Epstein-Barr Virus (EBV)-transformed B-lymphocytes to co-transform yeast reporter strain Y153 with pGBT$_{10}$-IFNAR1-IC. The yeast Y153 strain has two reporter genes under the control of GAL1 Upstream Activating Sequences (UAS) which are transcribed only if the activity of the Gal4 transcription factor is reconstituted. This requires that the fusion protein encoded by the pACT plasmid which was introduced into this particular yeast clone have affinity for the IFNAR1-IC domain from the pGBT10 plasmid. One of the reporter genes is GAL1 His3, which allows for growth in a medium lacking histidine; the other reporter gene is GAL-lacZ, which provides β-galactosidase activity. In addition, the pACT plasmids have the Leu2 gene and the pGBT$_{10}$ plasmid has the TRP1 gene which allows for growth in a medium lacking leucine and tryptophan, respectively. Colonies were selected in synthetic medium SC minus Trp, Leu, His in the presence of 25 mM 3-aminotriazole (which further selects for histidine prototrophy). The growing colonies were then tested for β-galactosidase activity using the X-gal filter assay (Breeden and Naysmith, 1985).

Nine positive yeast clones were obtained and their pACT plasmids were recovered by transfection into *E. coli* HB101 and selection for leu+ transformants. For each yeast DNA, two such *E. coli* HB101 clones were isolated. Partial DNA sequencing of the pACT plasmids from these *E. coli* clones showed that they fell into two groups of cDNA sequences which were designated IR1B1 and IR1B4. The pACT plasmids of the IR1B1 and IR1B4 groups were subjected to specificity tests by co-transformation of the SFY526 yeast reporter strain (Bartel et al, 1993) with pAS plasmids harboring lamin, cdk2 and p53 or other control inserts (CloneTech). Colonies which grew in SC -trp, -leu were tested for β-galactosidase expression. From the specifically positive pACT plasmids, inserts were excised with XhoI, cloned into BS—KS (Stratagene) and subjected to sequencing from T7 and T3 promoters using the DyeDeoxy Terminator Cycle Sequencing Kit in a 373A DNA Sequencer (Applied Biosystems).

FIG. 1 shows the results for pACT clone IR1B1 co-transfected into yeast SFY526 with different pAS or pGBT$_{10}$ plasmid baits. Yeast cells grew in the selective SC medium -trp, -leu in streaks 1 to 9 of the filter. Staining by X-gal reagent (5-bromo-4-chloro-3-indolyl-β-D-galactopyranoside) was positive only in streaks 2 and 4. As indicated in FIG. 1, streak 4 is a control yeast with an active lacZ gene. Streak 2 is the combination of IR1B1 and IFNAR1-IC fusion proteins. IR1B1 alone (streak 9), or any other combination besides IR1B1 and IFNAR1-IC, did not exhibit β-galactosidase activity. Therefore, IR1B1 is specifically able to combine with the IC domain of the IFNAR1 IFN receptor chain.

Similarly, FIG. 2 shows the results for pACT clone IR1B4 co-transfected into yeast SFY526 with different pAS or pGBT$_{10}$ plasmid baits. Yeast cells grew in SC medium trp, leu in streaks 1 to 8 of the filter and staining by Xgal reagent was positive only in streaks 3 and 7. As indicated in the lower boxed portion of FIG. 2, streak 7 is a control yeast with an active lacZ gene. Streak 3 is the combination of IR1B4 and IFNAR1-IC fusion proteins. Like the results obtained with IR1B1, IR1B4 alone (streak 1), or any other combination besides IR1B4 and IFNAR1-IC, did not exhibit β-galactosidase activity. Therefore, IR1B4 is also specifically able to combine with the IC domain of the IFNAR1 IFN receptor chain.

EXAMPLE 2

IR1B1 Protein Sequence Shows Calcium-Binding EF Hand Sites

The cDNA insert of the pACT-IR1B1 plasmids was excised with restriction enzyme XhoI, cloned into a Bluescript BS-KS vector and subjected to sequencing from T7 and T3 promoters using the DyeDeoxy Terminator Cycle Sequencing kit in a 373A DNA sequencer (Applied Biosystems). The longest plasmid had a sequence of 830 nucleotides (FIG. 3) following the Gal4 Activation domain and linker sequence of the pACT plasmid and an open reading frame of 191 amino acids was found therein (FIG. 3). An online search of the protein databases was performed using the Blast algorithm (Altschul et al, 1990) as well as the Bioaccelerator Alignment (Henikoff and Henikoff, 1992). The highest scores were obtained for caltractin (CATR_HUMAN, accession Swiss Protein SW New P41208) with 62.1 1% similarity and 32.4% identity from amino acids 52 to 173, and for calcineurin B (CALB NAEGR, accession Swiss Protein P42322; CALB_HUMAN, accession P06705) with 59.8% similarity and 32.5% identity from amino acids 50 to 171.

FIG. 4 shows the alignment of IR1B1 with human calcineurin B (CALB) and caltractin (CATR). The calcium binding, helix-loop-helix EF-hand domains are shown in bold and underlined characters. IR1B1 has two EF-hand sites but the first two EF-hand domains are not conserved. IR1B1 shows homology to both calcineurin B (represented by vertical lines in FIG. 4) and caltractin (represented by colons in FIG. 4). However, IR1B1 is clearly a novel and different human protein which has not been previously identified.

EXAMPLE 3

IR1B1 is an IFN-Induced Gene Product

Human myeloma U266S cells (about $3 \times 10^6$ cells in 5 ml suspension cultures) were treated with recombinant IFN-α8 ($2 \times 10^8$ IU/mg from bacteria) or with recombinant IFN-β ($3 \times 108$ IU/mg from CHO cells) at 750 IU/ml for 2 hours or for 18 hours. After treatment with IFN, the cells were collected and extracted with Tri-reagent (Molecular Research Center, Cincinnati, Ohio), which is a product containing guanidinium thiocyanate and phenol. The extracted RNA was ethanol precipitated, denatured with formaldehyde, analyzed by electrophoresis in formaldehyde-agarose gels (10 µg RNA/slot), and blotted on Gene-Screen Plus (Dupont, New England Nuclear, Billerica, Mass.). The Northern blot was reacted with 106 cpm of IR1B1 cDNA labeled with the Rediprime kit (Amersham, UK) using $^{32}$P-dCTP and random priming.

Figure 5:
FIG. 5 shows Northern blots of IR1B1 mRNA and 18S rRNA (lower line) in human myeloma U266S cells hybridized to IR1B1 cDNA and the rapid and transient induction of IR1B1 upon treatment of the cells with either IFN-α8 or IFN-β for 2 hrs. or 18 hrs. The first line is a control without IFN treatment after 2 hrs.

FIG. 5 shows that the IR1B1 cDNA hybridized to a 1.1 kb RNA. The amount of IR1B1 mRNA was markedly increased 2 hours after IFN-β treatment of U266S cells. However, at 18 hours after IFN treatment, the IR1B1 mRNA had disappeared from the cells, indicating that the induction is both rapid and transient. Many IFN-induced mRNAs continue to accumulate in the cells for over 24 hours after IFN treatment (Revel and Chebath, 1986).

It was verified that the same amount of RNA was present in each lane. As shown on the lower part of FIG. 5, hybridization of the same U266S (rich in IFN receptor) RNA to an 18S ribosomal cDNA probe reveals the same amount of 18S rRNA in each lane (only the part of the blot where 18S rRNA runs is shown). In another experiment using 1,200 U/ml of IFN for induction, IR1B1 mRNA was also observed with IFN-α8 at 2 hours, but not at 30 minutes (not shown).

The IR1B1 mRNA was found to have the same 1.1 kb size in different human cells (U266, Daudi and THP-1 cells). It is notable that this size is close to that of caltractin mRNA but not to that of calcineurin B mRNA (2.5 kb). The small size of the mRNA is consistent with IR1B1 being a small protein of about 20 kDa.

EXAMPLE 4

IR1B4 Protein Binds to IFNAR1 in Vitro

The binding of IR1B4 to the IC-domain of IFNAR1 was tested by synthesizing the IR1B4 protein with a protein tag (flag sequence) using in vitro translation in reticulocyte lysates and reacting this protein with a recombinant IFNAR1-IC fusion protein in *E. coli*. The pact-IR1B4 DNA from Example 1, cut with XhoI and filled-in by Klenow enzyme, was cloned in the PECE-flag expression vector (Ellis et al, 1986) cut with EcoRI and filled-in. The NotI-BamHI fragment containing the in-frame flag-IR1B4 fusion was recloned in BS-SK cut with NotI-BamHI and downstream from the T3 promoters. The sequence of the flag fusion was verified by sequencing from the T3 promoter. In vitro transcription (Promega kit) was done with T3 polymerase and 1 µg of BamHI-linearized BS-flag-IR1B4 DNA. In vitro translation was carried out in rabbit reticulocyte lysates (Promega kit) with [$^{35}$S]methionine (Amersham) and 5 µg of RNA transcripts for 1 h. at 30° C. The products were RNase treated before use. The GST-IFNAR1-IC fusion protein was prepared by cloning the BamHI-EcoRI, insert of BS-IFNAR1-IC (see above) into the same sites of pGEX2 (Pharmacia Biotech). GST and GST-IFNAR1-IC were expressed in *E. coli* and recovered bound to Glutathione-Agarose beads (Sigma).

Anti-flag M2 agarose beads were from Kodak Scientific Imaging Systems. Monoclonal antibodies IFNaR3 to the α-component of the IFN receptor (IFNAR1) were a kind gift of Dr. O. Colamonici (Colamonici et al, 1990) and were used at 1:100 dilution. Rabbit antibodies to the C-terminal peptide of IFNAR1-IC (Ab 631) were prepared and used for immunoprecipitation of IFNAR1 from Brij extracts (0.75 ml) of 2×10$^7$ human myeloma U266S and U266R cells with antiproteases previously detailed (Abramovich et al, 1994) except that protein G beads (Pharmacia) were used with mAb IFNaR3 SDS-PAGE and analysis in a Fujix BAS1000 Phosphor Imager were as before (Harroch et al, 1994).

Figure 6A:
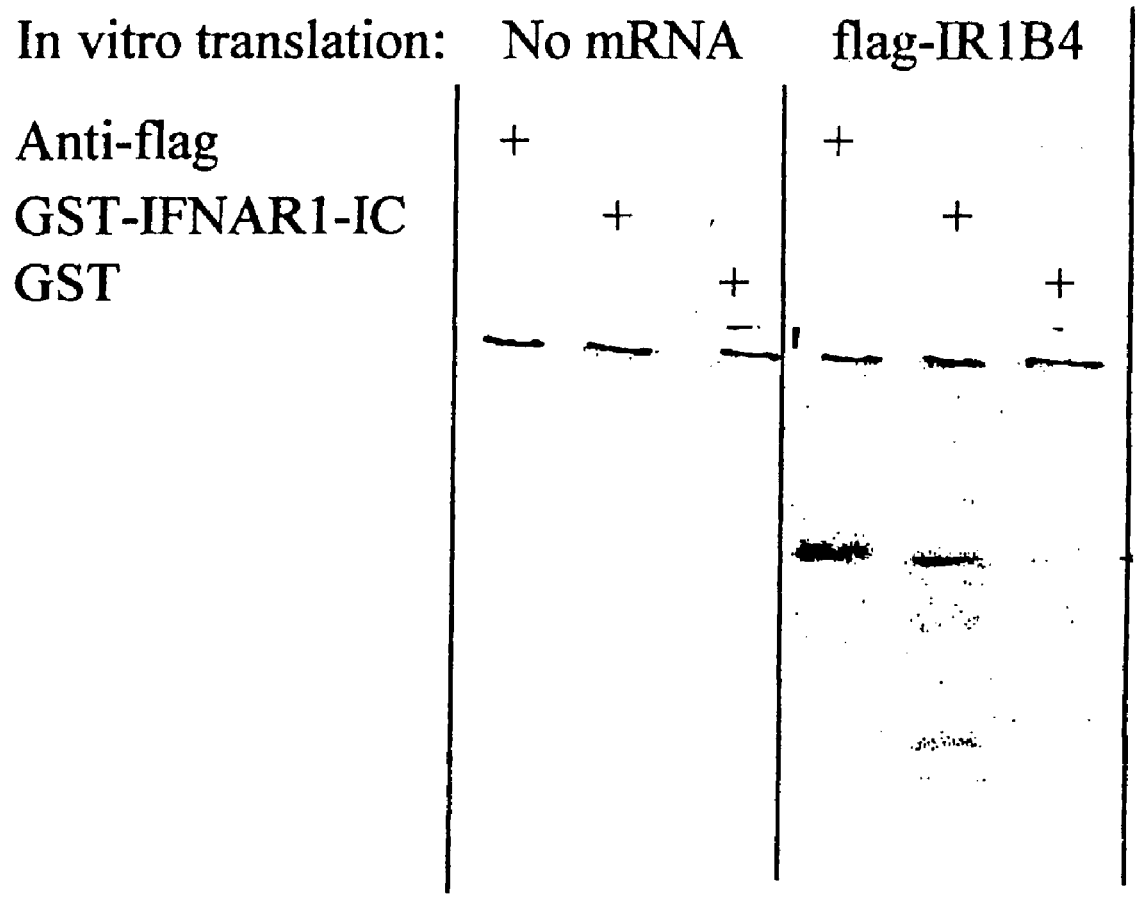
FIGS. 6A and 6B are SDS-PAGE lanes showing the in vitro interaction of IR1B4 with the isolated IFNAR1-IC domain (FIG. 6A) and with cell extracts from human U266S and U266R cell membranes (FIG. 6B).
Figure 6B:
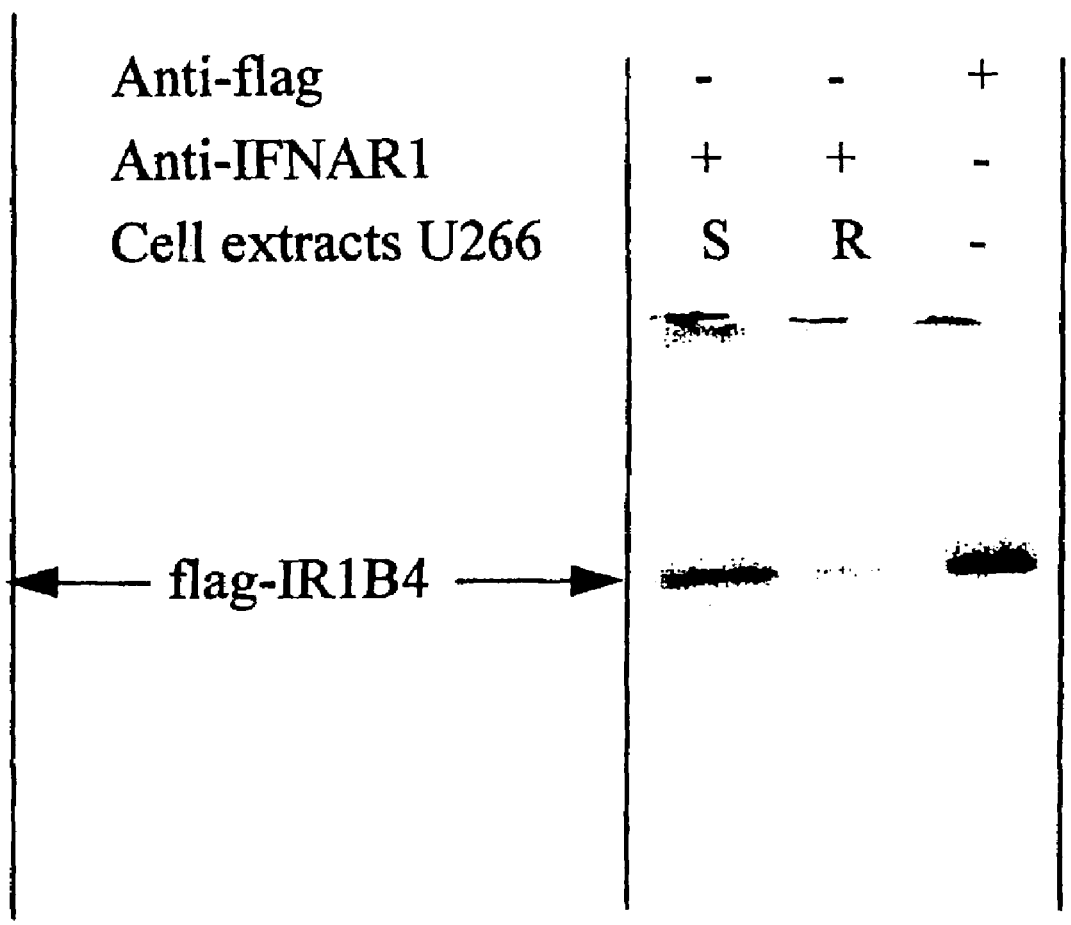

It was first verified that a protein product of about 32 kDa is obtained when the translation products were immunoprecipitated by anti-flag antibodies (FIGS. 6A and 6B). In FIGS. 6A and 6B, whenever the use of anti-flag antibodies is noted (by+sign), it means that the radioactive translation product of the IR1B4-flag fusion mRNA (in vitro transcribed from the corresponding DNA construct) was reacted with anti-flag M2 antibody bound to agarose beads (product of Kodak Scientific Imaging Systems). The translated protein which contains IR1B4 fused to the flag amino acid sequence was bound to these anti-flag antibody beads and after centrifuging down the beads, the protein was eluted with SDS buffer and applied onto SDS-PAGE. These reactions serve as a control to demonstrate that the expected fused protein is present.

Beads of Glutathione-Sepharose (Sigma), to which the Glutathione S-transferase (GST) fused to IFNAR1-IC was bound, were added to the reticulocyte lysate translation reaction. The beads were centrifuged and washed and the proteins bound to GST beads were released by sodium dodecyl sulfate (SDS 1%) and analyzed by SDS-polyacrylamide gel electrophoresis (PAGE). The 32 kDa protein labeled by $^{35}$S-methionine was observed to be bound to GST-IFNAR1-IC but not to GST alone (FIG. 6A). This demonstrates that IR1B4 directly binds to the isolated IFNAR1-IC peptide region.

To verify that IR1B4 interacts with the IFNAR1 protein as present in human cell membranes, detergent extracts of human myeloma U266 cells were mixed with the $^{35}$S-methionine labeled translation products of IR1B4 mRNA from reticulocyte lysates. The IFNAR1 protein was immunoprecipitated by a monoclonal antibody IFNaR3 specific to the ectodomain of IFNAR1 (from Colamonici et al, 1990). Analysis by SDS-PAGE showed the presence of the 32 kDa IR1B4-flag band (FIG. 6B) when the detergent extracts originated from U266S (rich in IFN receptor), but not when originating from U266R cells—a mutant IFN-α, β-resistant derivative cell line from U266 deficient in IFN receptors (Abramovich et al, 1994). The 32 kDa band similarly was seen when U266S extracts were reacted with Ab 631 against the C-terminal peptide of IFNAR1, and IFNAR1 was precipitated by anti-flag when Cos-7 cells were transferred by flg-IR1B4 and human IFNAR1 cDNAs. These results demonstrated that IR1B4 binds to intact IFNAR1 from human cells in a specific manner.

EXAMPLE 5

IR1B4 cDNA and Protein Sequences

The nucleotide sequence of the IR1B4 cDNA has an open reading frame encoding a 361 amino-acid long protein (FIG. 7). This human cDNA recognized a 1.5 kb constitutively expressed poly-A$^+$ mRNA in various human cells including U266 myeloma cells. An online search of the protein databases was performed using the BlastP algorithm (Altschul et al, 1990) as well as the Bioaccelerator Alignment (Henikoff and Henikoff, 1992), and it was found that IR1B4 is a unique member of the protein-arginine methyltransferase family. The rat PRMT1 cDNA described by Lin et al (1996, Genbank sequence I.D. 1390024; Accession U60882) is only 81.4% homologous when analyzed by the ALIGN computer program. At the amino acid level (FIG. 8), the human IR1B4/PRMT differs clearly in its amino terminus from PRMT1, with the first 19 amino acids being completely different. N-terminal sequencing of IR1B4 alone would not have provided any indication that IR1B4 is homologous to PRMT1. Another human protein which has been described, HCP-1 (Nikawa et al, 1996; Genbank accession D66904) was also found to have homology to IR1B4. However, HCP-1 has a different amino acid sequence from residues 147–175 (FIG. 9). HCP-1 was originally identified based on its ability to complement the irel5 mutation in yeast and its enzymatic function was not previously identified (Nikawa et al, 1996). Therefore, IR1B4 is a novel human protein.

EXAMPLE 6

IR1B4 Protein Bound to IFNAR1-IC Has Methyltransferase Activity

Figure 10:
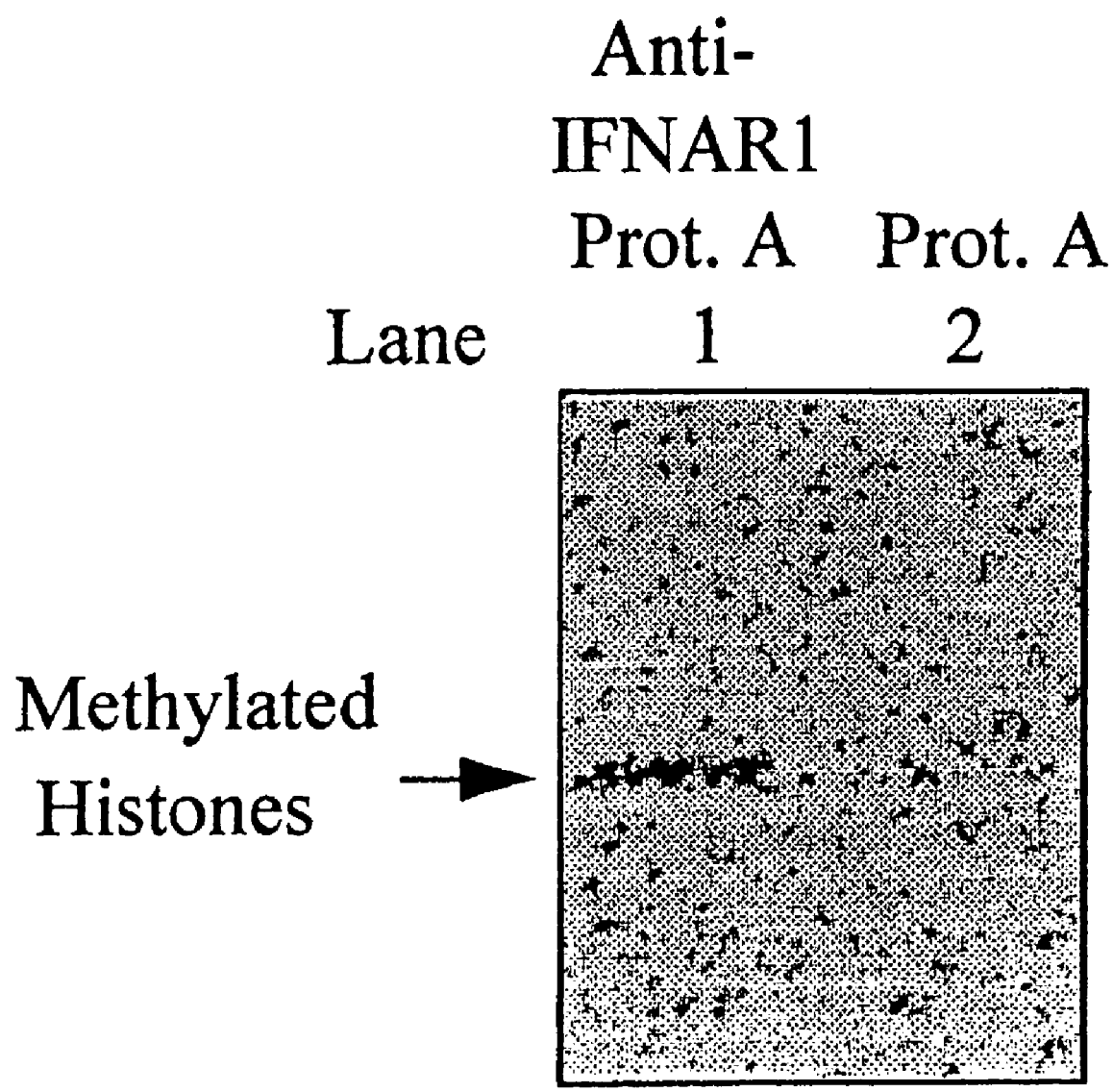
FIG. 10 shows a methyltransferase assay. Extract of U266S cells were reacted with beads coated with Protein A and anti-IFNAR1 antibody (lane 1) or with Protein A alone (lane 2). Methyltransferase activity was measured by labeling of histones with $^{14}$C(methyl)-S-adenosyl methionine and analyzing radioactivity in the histone band by electrophoresis on SDS-PAGE.

Methyltransferase activity could be co-immunoprecipitated from human cell extracts with the IFNAR1 receptor. Brij-detergent extracts of U266S cells were reacted overnight at 4° C. with or without anti-IFNAR1 antibody Ab 631 (Abramovich et al, 1994). Protein A beads (40 µl of a 50% of IPA-400 fast flow, Repligen) were added for 1 hour. The beads were washed and incubated in 0.1 ml of 25 mM Tris-HCl, pH 7.5, 1 mM EDTA, 1 mM EGTA, 50 µM (0.25 µCi) $^{14}$C-(methyl)-S-adenosyl-methionine (Amersham), and 100 µg histones (Type IIA from calf thymus, Sigma) for 30 min. at 30° C. The in vitro methylation of histones was carried out under the conditions described by Lin et al (1996). The radioactivity in the histone band was analyzed after SDS PAGE (15% acrylamide) and exposure in the Phosphor-imager. A $^{14}$C-methyl labeling of the histones was observed with the beads that were coated with anti-IFNAR1, but not with those in the control reaction (FIG. 10). Therefore, protein methyl-transferase activity is constitutively associated with the IFN receptor chain of these human cells. A similar enzyme activity was recovered when IFNAR1 was immunoprecipitated five minutes after addition of IFN-β to the U266S cells.

EXAMPLE 7

Involvement of IR1B4/PRMT1 in IFN Action

Figure 11:
FIG. 11 shows an assay of protein-arginine methyltransferase activity in U266S cells. In lane 1, the protein-arginine methyltransferase activity of human U266S cells was measured by methylation of peptide R1, having the sequence of SEQ ID NO:11. In lane 2 an anti-sense oligonucleotide of SEQ ID NO:12, complementary to the sequence of nucleotides 12–33 around the initiation codon of IR1B4 cDNA, was added. In lane 3 the corresponding sense oligonucleotide was added. It is seen that the anti-sense oligonucleotide substantially inhibits the protein-arginine methyltransferase activity while the control sense oligonucleotide has little effect.
Figure 12:
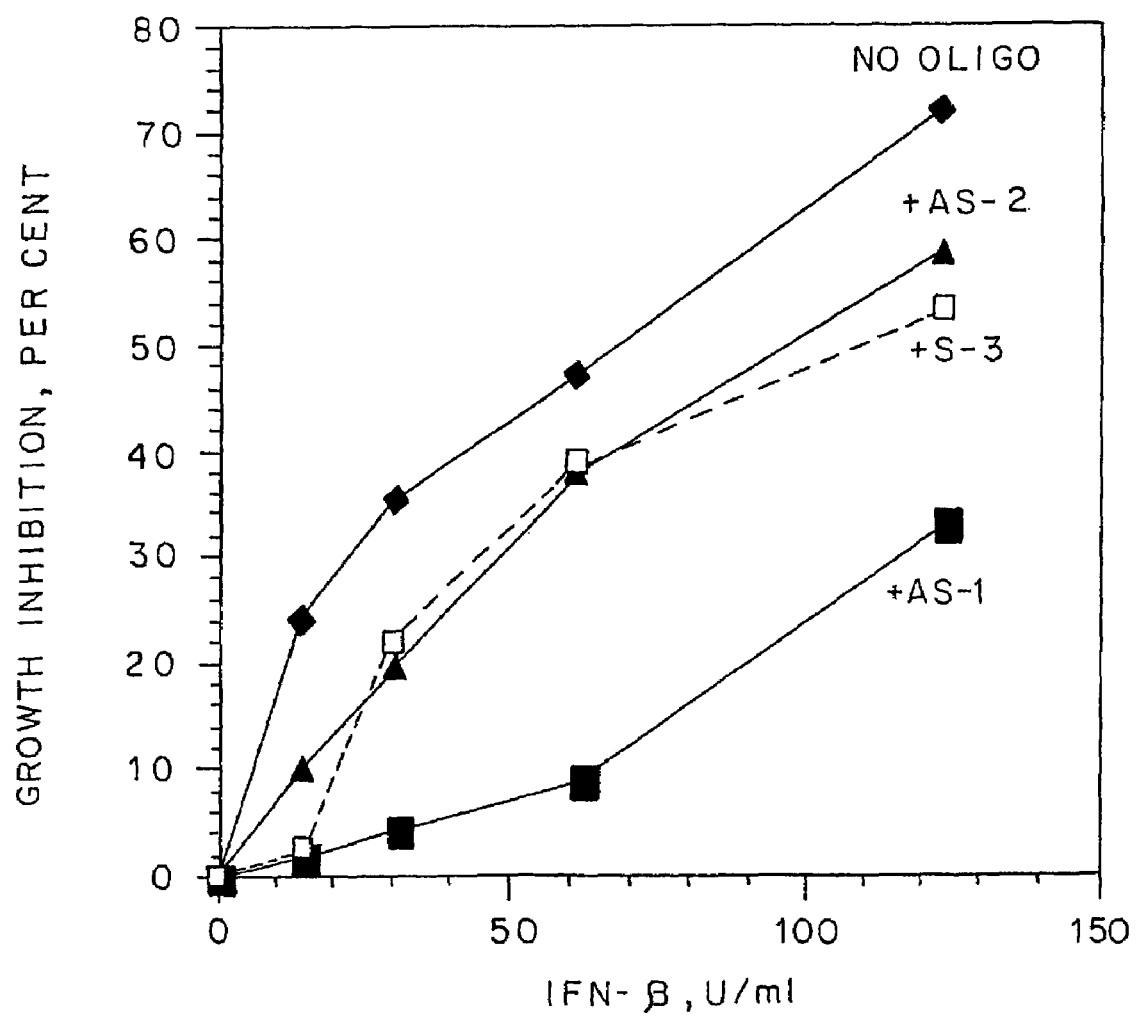
FIG. 12 is a graph showing the growth inhibition of human U266S cells in response to IFN-β treatment in the presence or absence of the anti-sense oligonucleotide used in FIG. 11 (AS-1), the corresponding sense oligonucleotide (S-3), and another anti-sense oligonucleotide directed to the middle of IR1B4 cDNA (AS-2). Cell density was quantitated by a color test with Alamar Blue (see Example 7) and the reduction in cell density was calculated in percent of control wells untreated, and plotted as growth inhibition.

An antisense oligodeoxynucleotide phosphorothioate (Stein et al, 1989) complementary to the sequence of nucleotides 12–33 around the initiation codon of IR1B4 cDNA (AS-1, anti-sense sequence 5'GGCTACAAAATTCTCCATGATG-3'; SEQ ID NO:12) was synthesized chemically. The oligonucleotides were added to U266S cells seeded in 96-well microplates (8000 cells/well/0.2 ml RPMI, 10% FCS) at a final concentration of 10 µM on day 0 and re-added at 5 µM on day 2. IFN-β was added at 64 or 125 IU/ml on day 0. After 3 days of culture, 20 µl of Alamar Blue, a colorimetric cell density indicator based on oxido-reduction (BioSource, Camarillo, Calif.), was added to each well and incubation continued for 6–7 h. Color was measured in a microplate ELISA reader (test filter 530 nm, reference filter 630 nm) with multiple reading of duplicate wells. Correlation of the growth curves by live cell number and by OD was verified. To measure methyltransferase, cells from pooled wells were lysed by freeze-thawing in 25 µl/well of 25 mM Tris-HCl, pH 7.4, 1 mM EDTA, 1 mM EGTA, 40 µg/ml leupeptin and aprotinin, 20 µg/ml pepstatin, 1 UM phenylmethylsulfonyl fluoride (PMSF). Reactions were in 50 µl with 25 µl of cell extracts, 100 µM peptide R1 (Najbauer et al, 1993; obtained from Genosys, Cambridge, UK), 3 µCi of [$^3$H] (methyl)S-adenosylmethionine (Amersham, 73 Ci/mmol) for 30 min at 30° C. After electrophoresis in SDS-polyacrylamide (16%) gel, fixation in 50% methanol, 10% acetic acid and treatment by Amplify (Amersham), autoradiography was carried out for 8 days. This AS-1 anti-sense DNA was able to strongly reduce the protein-arginine methyltransferase activity in U266S cells as measured by incorporation of tritiated-methyl groups to the R1 peptide substrate (FIG. 11), and was used to investigate the role that this enzyme may play in IFN action. The growth-inhibitory activity of IFN was chosen because it can be most directly quantified on cells and because an interaction of rat PRMT1 with growth-related gene products has been observed (Lin et al, 1996). Addition of the antisense-1 oligonucleotide AS-1, which is complementary to the sequence around the initiation codon of IR1B4/PRMT cDNA, reduced the growth inhibitory effect of IFN-β on human myeloma U266S cells (FIG. 12). This means that, in the presence of anti-sense AS-1, the IFN-treated cells exhibited a higher growth (excluding any toxic effect of phosphorothioates). The growth in the absence of IFN was not significantly affected. The sense oligonucleotide S-3 corresponding to the same cDNA region had only a small effect (S-3, FIG. 12) as compared to antisense-1. Sense S-3 also had only a slight inhibitory effect on the level of enzyme activity (FIG. 11). Another anti-sense phosphorothioate oligonucleotide AS-2 (SEQ ID NO:13), directed to the middle of the cDNA and complementary to nucleotides 572–592 of SEQ ID NO:7, had almost no effect (FIG. 12). The up to 5 fold reduction in the growth inhibitory effect of IFN-β on myeloma cells, which were rendered partially deficient in PRMT activity by antisense-1 oligonucleotide demonstrates that the association of the IR1B4/PRMT enzyme with the IC domain of the IFNAR1 receptor is functionally significant for IFN action on cells.

These experiments also demonstrate that the IR1B4 protein methylates peptide substrates of the PRMT class of enzymes, such as the R1 peptide Gly-Gly-Phe-Gly-Gly-Arg-Gly-Gly-Phe-Gly (SEQ ID NO:11; Najbauer et al, 1993), which was used in the experiment illustrated in FIG. 11.

Methylation of proteins on arginine residues next to glycine residues (e.g., as in the above peptide) could be a type of protein modification which, like phosphorylation, serves to transduce signals into the cell. The hnRNP group of proteins is a target for PRMT enzymes, and since these proteins affect mRNA processing, splicing, transport and stability (Liu and Dreyfuss, 1995), their methylation may play a role in post-transcriptional controls of gene expression. The IR1B4/PRMT protein, discovered here as binding to a chain of the IFN receptor, could mediate changes in gene expression in response to IFN. Other protein substrates may become methylated through the IFN receptor, including other components of the IFN receptor complex and transcription factors. Lin et al (1996) have observed that the binding of rat PRMT1 to growth factor-induced proteins activates PRMT1 and modifies its substrate specificity, possibly by removal of some inhibitory proteins associated with PRMT1 in the cytoplasm of cells. A similar activation of IR1B4 bound to the IFNAR1 chain of the IFN receptor can be expected.

CONCLUSIONS

A new protein IR1B1 is described which interacts with the intracytoplasmic domain of the IFNAR1 chain of the type I interferon receptor. This protein is induced very rapidly and transiently following IFN treatment of human cells. IR1B1 is characterized by the presence of helix-loop-helix EF-handle sites which are the hallmark of calcium-binding proteins. Calcium ion fluxes have been implicated in the mechanism of action of IFNs, and in particular for the initial cell responses and changes in cell morphology and in cytoskeleton organization (Tamm et al, 1987). Calcium ion-activated enzymes could produce second messengers, such as diacyl-glycerol, in response to IFNs. Furthermore, calmodulin-like proteins regulate a number of protein kinases and these pathways have been observed to function in IFN-treated cells (Tamm et al, 1987). It is likely that the IFN receptor binding protein IR1B1 is involved in such $Ca^{++}$-dependent effects of IFNs on cells.

The two-hybrid screening for proteins interacting with the IFNAR1-IC domain also identified another protein IR1B4, which turned out to be a member of the protein-arginine methyl transferase family of enzymes (PRMT1; Lin et al, 1996). This enzyme is known to methylate a number of RNA and DNA binding proteins, in particular heterologous nuclear ribonucleoproteins (hnRNPs). The hnRNPs are involved in mRNA transport from nucleus to cytoplasm, alternative splicing of pre-mRNA, and post-transcriptional controls (Liu and Dreyfuss, 1995). The IR1B1 and IR1B4/PRMT1 proteins which dock onto the IFNAR1-IC domain reveal novel signaling mechanisms of IFNs that exist besides the known Jak-Stat pathways described by Darnell et al (1994).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Abramovich et al, "Differential tyrosine phosphorylation of the IFNAR chain of the type I Interferon receptor and of an associated surface protein in response to IFN-α and IFN-β", EMBO J 13:5871–5877 (1994)

Altschul et al, "Basic local alignment research tool", J Mol Biol, 215:403–410 (1990)

Barter et al, "Elimination of false positives that arise in using the two-hybrid system", BioTechniques 14:920 924 (1993)

Boldin et al, "A novel protein that interacts with the death domain of Fas/APO1 contains a sequence motif related to the death domain. J Biol Chem 270:7795–7798 (1995)

Breeden and Naysmith, "Regulation of the yeast HO gene", Cold Spring Harbor Symp Ouant Biol 50:643–650 (1995)

Colamonici et al, "Characterization of three monoclonal antibodies that recognize the Interferon-2 receptor", Proc Natl Acad Sci USA 87:7230–7234 (1990)

Darnell et al, "Jak-Stat pathways and transcriptional activation in response to IFNs and other extracellular signaling proteins", Science 264:1415–1421 (1994)

David et al, "Differential regulation of the alpha/beta Interferon-stimulated Jak/Stat pathway by the SH2 domain-containing tyrosine phosphatase SHPTP1" Mol Cell Biol 15:7050–7058 (1995a)

David et al, "Requirement for MAP kinase (ERK2) activity in Interferon α- and Interferon β-stimulated gene expression through Stat proteins", Science 269:1721–1723 (1995b)

David et al, Activation of Protein kinase A inhibits Interferon induction of the Jak/Stat pathway in U266 cells", J Biol Chem 271:4585–4588 (1996)

Deiss and Kimchi, "A genetic tool used to identify thiroredoxin as a mediator of a growth inhibitory signal", Science 252:117–120 (1991)

Domanski et al, "Cloning and expression of a long form of the beta subunit of the Interferon alpha beta receptor that is required for signaling", J Biol Chem 270:21606–21611 (1995)

Durfee et al, "The retinoblastoma protein associates with the protein phosphatase type 1 catalytic subunit", Genes & Devout 7:555–569 (1993)

Ellis et al, Replacement of insulin receptor tyrosine residues 1162 and 1163 compromises insulin-stimulated kinase activity and uptake of 2-deoxyglucose", Cell 45:721–731 (1986)

Fields and Song, "A novel genetic system to detect protein-protein interactions", Nature 340:245–246 (1989).

Guerini et al, "Isolation and sequence of a cDNA clone for human calcineurin B, the Ca2+-binding subunit of the Ca2+/calmodulin-stimulated protein phosphatase", DNA 8:675–682 (1989).

Harroch et al, "Interleukin-6 signaling via four transcription factors binding palindromic enhancers of different genes", J Biol Chem 269:26191–26195 (1994)

Henikoff and Henikoff, "Amino acid substitution matrices from protein blocks", Proc Natl Acad Sci USA, 89:10915–10919 (1992)

Kagan and Clarke, "Widespread occurrence of three sequence motifs in diverse S-adenosyl methionine-dependent methyltransferases suggests a common structure for these enzymes", Arch Biochem Biophys 310:417–427 (1994)

Lee, V. D. and Huang, B. Proc Natl Acad Sci USA 90:11039–11043 (1993)

Leung et al, "Role of Stat2 in the alpha Interferon signaling pathway", Mol Cell Biol 15:1312–1317 (1995)

Lin et al, "The mammalian immediate-early TIS21 protein and the leukemia-associated BTG1 protein interact with a Protein-arginine Methyltransferase", J Biol Chem 271: 15034–15044 (1996)

Liu And Dreyfuss "In vivo and in vitro arginine methylation of RNA-binding proteins", Mol Cell Biol 15:2800–2808 (1995)

Najbauer et al, "Peptides with sequences similar to glycine arginine rich motifs in proteins interacting with RNA are efficiently recognized by methyltransferases modifying arginine in numerous proteins", J Biol Chem 268, 10501–10509 (1993)

Nikawa et al, "Structural and functional conservation of human yeast HCPI genes which can suppress the growth defect of the Saccharomyces cerevisiae irel5 mutant", Gene 171:107–111 (1996)

Revel M, "The Interferon system in man: nature of the Interferon molecules and mode of action", In Antiviral Drugs and Interferon. The molecular basis of their activity, Becker, I. (ed.), Martinus Nijhoff Publ., Boston, pp 357–433 (1984).

Revel and Chebath, "Interferon-activated genes", Trends Biochem Sci 11:166–170 (1986)

Stein et al, "Physicochemical properties of phosphorothionate oligodeoxynucleotides", Nucleic Acids Res 6:3209–3221 (1989)

Tamm et al, "Interferons OL and ss as cellular regulatory molecules", In Interferon 9, Gresser, I. (ed.), Acad. Press, London, pp 14–74 (1987)

Uze et al, "Genetic transfer of a functional human Interferon a receptor into mouse cells: cloning and expression of its cDNA", Cell 60:225–234 (1990)

Wickstrom E, In: *Prospects for Antisense Nucleic Acid Therapy of Cancer and AIDS*, Wiley-Liss, New York, pp. 7–24 (1991).

Yang et al, "Direct association of Stat3 with the TFNAR-1 chain of the human type I Interferon receptor", *J Biol Chem* 271:8057–8061 (1996).

What is claimed is:

1. An isolated recombinant DNA molecule comprising a nucleotide sequence encoding a protein having the amino acid sequence of SEQ ID NO:2.

2. An isolated recombinant DNA molecule in accordance with claim 1, further comprising a promoter operably-linked to said nucleotide sequence such that said promoter promotes the transcription of said nucleotide sequence when the recombinant DNA molecule is in an appropriate expression host.

3. An isolated recombinant DNA molecule according to claim 2, wherein said promoter is a constitutive promoter in human cells.

4. An isolated recombinant DNA molecule in accordance with claim 1, wherein said nucleotide sequence is SEQ ID NO:1.

5. An expression vector comprising a recombinant nucleic acid molecule comprising a DNA molecule, of SEQ ID NO: 1 operably-linked in the anti-sense orientation to a promoter.

6. An expression vector according to claim 5, wherein said nucleotide sequence of SEQ ID NO: 1, when in the sense orientation, includes the initiation codon at the 5'-end of SEQ ID NO: 1.

7. An isolated recombinant DNA molecule according to claim 2, wherein said promoter is an interferon-inducible promoter.

8. An isolated recombinant DNA molecule according to claim 1, which is an expression vector.

9. An isolated host cell which includes an expression vector in accordance with claim 8.

10. A method for producing a protein having the amino acid sequence of SEQ ID NO:2, comprising culturing a host cell transfected with a vector containing the DNA molecule of claim 1, and isolating the protein expressed thereby.

11. An isolated anti-sense RNA molecule which corresponds to a DNA molecule comprising the nucleotide sequence of SEQ ID NO: 1 in the anti-sense orientation.

* * * * *